(12) United States Patent
Pollock

(10) Patent No.: US 9,254,288 B2
(45) Date of Patent: Feb. 9, 2016

(54) SUSCEPTIBILITY OF TUMORS TO TYROSINE KINASE INHIBITORS AND TREATMENT THEREOF

(71) Applicant: Pamela Michelle Pollock, Queensland (AU)

(72) Inventor: Pamela Michelle Pollock, Queensland (AU)

(73) Assignees: THE TRANSLATIONAL GENOMICS RESEARCH INSTITUTE, Phoenix, AZ (US); QUEENSLAND UNIVERSITY OF TECHNOLOGY, Queensland (AU)

( * ) Notice: Subject to any disclaimer, the term of this patent is extended or adjusted under 35 U.S.C. 154(b) by 129 days.

(21) Appl. No.: 13/889,337

(22) Filed: May 7, 2013

(65) Prior Publication Data
US 2013/0296326 A1 Nov. 7, 2013

Related U.S. Application Data

(60) Provisional application No. 61/643,532, filed on May 7, 2012.

(51) Int. Cl.
| | |
|---|---|
| *A61K 31/495* | (2006.01) |
| *A61K 31/506* | (2006.01) |
| *A61K 31/5025* | (2006.01) |
| *A61K 31/496* | (2006.01) |
| *A61K 31/4709* | (2006.01) |
| *C12Q 1/68* | (2006.01) |
| *A61K 31/497* | (2006.01) |
| *A61K 31/51* | (2006.01) |

(52) U.S. Cl.
CPC ........... *A61K 31/506* (2013.01); *A61K 31/4709* (2013.01); *A61K 31/496* (2013.01); *A61K 31/497* (2013.01); *A61K 31/5025* (2013.01); *A61K 31/51* (2013.01); *C12Q 1/6886* (2013.01); *C12Q 2600/112* (2013.01); *G01N 2800/52* (2013.01)

(58) Field of Classification Search
USPC ........................ 514/248, 252.14, 254.05, 314
See application file for complete search history.

(56) References Cited

U.S. PATENT DOCUMENTS

| 8,114,874 B2 * | 2/2012 | Zou et al. ...................... 514/248 |
| 2009/0137804 A1 * | 5/2009 | Ding et al. .................... 544/329 |
| 2011/0275084 A1 * | 11/2011 | Byron et al. ................. 435/6.12 |

FOREIGN PATENT DOCUMENTS

WO WO2011053948 * 5/2011

OTHER PUBLICATIONS

Gavine et al., Cancer Research, 72(8): 20452056, Feb. 27, 2012.*
Usui's CAS: 154: 449852, 2011.*

* cited by examiner

*Primary Examiner* — Rei-Tsang Shiao

(57) ABSTRACT

This disclosure provides tyrosine kinase protein and nucleic acid variants, particularly FGFR2 variants, which are linked to drug resistance. The disclosure further provides methods of diagnosis and theranosis, using these molecules and fragments thereof, and kits for employing these methods and compositions.

12 Claims, 12 Drawing Sheets

```
                               SEQUENCE LISTING

<160> NUMBER OF SEQ ID NOS: 2

<210> SEQ ID NO 1
<211> LENGTH: 4647
<212> TYPE: DNA
<213> ORGANISM: Homo sapiens
<220> FEATURE:
<221> NAME/KEY: misc_feature
<223> OTHER INFORMATION: fibroblast growth factor receptor 2 isoform 2
      precursor

<400> SEQUENCE: 1
ggcggcggct ggaggagagc gcggtggaga gccgagcggg cgggcggcgg gtgcggagcg      60
ggcgagggag cgcgcgcggc cgccacaaag ctcgggcgcc gcggggctgc atgcggcgta     120
cctggcccgg cgcggcgact gctctccggg ctggcggggg ccggccgcga gccccggggg     180
ccccgaggcc gcagcttgcc tgcgcgctct gagccttcgc aactcgcgag caaagtttgg     240
tggaggcaac gccaagcctg agtcctttct tcctctcgtt ccccaaatcc gagggcagcc     300
cgcgggcgtc atgcccgcgc tcctccgcag cctggggtac gcgtgaagcc cgggaggctt     360
ggcgccggcg aagacccaag gaccactctt ctgcgtttgg agttgctccc cgcaaccccg     420
ggctcgtcgc tttctccatc ccgacccacg cggggcgcgg gacaacaca ggtcgcggag      480 gagcgttgcc attcaagtga ctgcagcagc agcggcagcg cctcggttcc tgagcccacc     540
gcaggctgaa ggcattgcgc gtagtccatg cccgtagagg aagtgtgcag atgggattaa     600
cgtccacatg gagatatgga agaggaccgg ggattggtac cgtaaccatg gtcagctggg     660
gtcgtttcat ctgcctggtc gtggtcacca tgcaaccctt gtccctggcc cggccctcct     720
tcagtttagt tgaggatacc acattagagc cagaagagcc accaaccaaa taccaaatct     780
ctcaaccaga agtgtacgtg gctgcgccag gggagtcgct agaggtgcgc tgcctgttga     840
aagatgccgc cgtgatcagt tggactaagg atggggtgca cttggggccc aacaatagga     900
cagtgcttat tgggggagtac ttgcagataa agggcgccac gcctagagac tccggcctct     960
atgcttgtac tgccagtagg actgtagaca gtgaaacttg gtacttcatg gtgaatgtca    1020
cagatgccat ctcatccgga gatgatgagg atgacaccga tggtgcggaa gattttgtca    1080
gtgagaacag taacaacaag agagcaccat actggaccaa cacagaaaag atggaaaagc    1140
ggctccatgc tgtgcctgcg gccaacactg tcaagtttcg ctgcccagcc ggggggaacc    1200
caatgccaac catgcggtgg ctgaaaaacg ggaaggagtt taagcaggag catcgcattg    1260
gaggctacaa ggtacgaaac cagcactgga gcctcattat ggaaagtgtg gtcccatctg    1320
acaagggaaa ttatacctgt gtagtggaga tgaatacgg gtccatcaat cacacgtacc     1380
acctggatgt tgtggagcga tcgcctcacc ggcccatcct ccaagccgga ctgccggcaa    1440
atgcctccac agtggtcgga ggagactag agtttgtctg caaggtttac agtgatgccc     1500
agccccacat ccagtggatc aagcacgtgg aaaagaacgg cagtaaatac ggccccgacg    1560
ggctgcccta cctcaaggtt ctcaagcact cggggataaa tagttccaat gcagaagtgc    1620
tggctctgtt caatgtgacc gaggcggatg ctggggaata tatatgtaag gtctccaatt    1680 atataggggca ggccaaccag tctgcctggc tcactgtcct gccaaaacag caagcgcctg    1740
gaagagaaaa ggagattaca gcttcccag actacctgga gatagccatt tactgcatag    1800
gggtcttctt aatcgcctgt atggtggtaa cagtcatcct gtgccgaatg aagaacacga    1860
```

```
ccaagaagcc agacttcagc agccagccgg ctgtgcacaa gctgaccaaa cgtatccccc      1920
tgcggagaca ggtaacagtt tcggctgagt ccagctcctc catgaactcc aacaccccgc      1980
tggtgaggat aacaacacgc ctctcttcaa cggcagacac ccccatgctg cagggggtct      2040
ccgagtatga acttccagag gacccaaaat gggagtttcc aagagataag ctgacactgg      2100
gcaagcccct gggagaaggt tgctttgggc aagtggtcat ggcggaagca gtgggaattg      2160
acaaagacaa gcccaaggag gcggtcaccg tggccgtgaa gatgttgaaa gatgatgcca      2220
cagagaaaga cctttctgat ctggtgtcag agatggagat gatgaagatg attgggaaac      2280
acaagaatat cataaatctt cttggagcct gcacacagga tgggcctctc tatgtcatag      2340
ttgagtatgc ctctaaaggc aacctccgag aatacctccg agcccggagg ccacccggga      2400
tggagtactc ctatgacatt aaccgtgttc ctgaggagca gatgaccttc aaggacttgg      2460
tgtcatgcac ctaccagctg gccagaggca tggagtactt ggcttcccaa aaatgtattc      2520
atcgagattt agcagccaga aatgttttgg taacagaaaa caatgtgatg aaaatagcag      2580
actttggact cgccagagat atcaacaata tagactatta caaaaagacc accaatgggc      2640
ggcttccagt caagtggatg gctccagaag ccctgtttga tagagtatac actcatcaga      2700
gtgatgtctg gtccttcggg gtgttaatgt gggagatctt cactttaggg ggctcgccct      2760
acccagggat tcccgtggag gaacttttta gctgctgaa ggaaggacac agaatggata      2820
agccagccaa ctgcaccaac gaactgtaca tgatgatgag ggactgttgg catgcagtgc      2880
cctcccagag accaacgttc aagcagttgg tagaagactt ggatcgaatt ctcactctca      2940
caaccaatga ggaatacttg gacctcagcc aacctctcga acagtattca cctagttacc      3000
ctgacacaag aagttcttgt tcttcaggag atgattctgt tttttctcca gacccccatgc      3060 cttacgaacc atgccttcct cagtatccac acataaacgg cagtgttaaa acatgaatga      3120
ctgtgtctgc ctgtccccaa acaggacagc actgggaacc tagctacact gagcagggag      3180
accatgcctc ccagagcttg ttgtctccac ttgtatatat ggatcagagg agtaaataat      3240
tggaaaagta atcagcatat gtgtaaagat ttatacagtt gaaaacttgt aatcttcccc      3300
aggaggagaa gaaggtttct ggagcagtgg actgccacaa gccaccatgt aaccctctc      3360 acctgccgtg cgtactggct gtggaccagt aggactcaag gtggacgtgc gttctgcctt      3420
ccttgttaat tttgtaataa ttggagaaga tttatgtcag cacacactta cagagcacaa      3480
atgcagtata taggtgctgg atgtatgtaa atatattcaa attatgtata aatatatatt      3540
atatatttac aaggagttat tttttgtatt gattttaaat ggatgtccca atgcacctag      3600
aaaattggtc tctcttttt taatagctat ttgctaaatg ctgttcttac acataatttc      3660
ttaattttca ccgagcagag gtggaaaaat acttttgctt tcagggaaaa tggtataacg      3720
ttaatttatt aataaattgg taatatacaa aacaattaat catttatagt ttttttttgta      3780 atttaagtgg catttctatg caggcagcac agcagactag ttaatctatt gcttggactt      3840
aactagttat cagatccttt gaaaagagaa tatttacaat atatgactaa tttggggaaa      3900
atgaagtttt gatttatttg tgtttaaatg ctgctgtcag acgattgttc ttagacctcc      3960
taaatgcccc atattaaaag aactcattca taggaaggtg tttcattttg gtgtgcaacc      4020
ctgtcattac gtcaacgcaa cgtctaactg gacttcccaa gataaatggt accagcgtcc      4080
tcttaaaaga tgccttaatc cattccttga ggacagacct tagttgaaat gatagcagaa      4140
tgtgcttctc tctggcagct ggccttctgc ttctgagttg cacattaatc agattagcct      4200
gtattctctt cagtgaattt tgataatggc ttccagactc tttggcgttg gagacgcctg      4260
```

```
ttaggatctt caagtcccat catagaaaat tgaaacacag agttgttctg ctgatagttt    4320
tggggatacg tccatctttt taagggattg ctttcatcta attctggcag gacctcacca    4380
aaagatccag cctcatacct acatcagaca aaatatcgcc gttgttcctt ctgtactaaa    4440
gtattgtgtt ttgctttgga aacacccact cactttgcaa tagccgtgca agatgaatgc    4500
agattacact gatcttatgt gttacaaaat tggagaaagt atttaataaa acctgttaat    4560
ttttatactg acaataaaaa tgtttctaca gatattaatg ttaacaagac aaaataaatg    4620
tcacgcaact taaaaaaaaa aaaaaaa                                        4647
```

<210> SEQ ID NO 2
<211> LENGTH: 822
<212> TYPE: PRT
<213> ORGANISM: Homo sapiens
<220> FEATURE:
<221> NAME/KEY: MISC_FEATURE
<223> OTHER INFORMATION: fibroblast growth factor receptor 2 isoform 2
      precursor <400> SEQUENCE: 2

```
Met Val Ser Trp Gly Arg Phe Ile Cys Leu Val Val Thr Met Ala
1               5                   10                  15

Thr Leu Ser Leu Ala Arg Pro Ser Phe Ser Leu Val Glu Asp Thr Thr
            20                  25                  30

Leu Glu Pro Glu Glu Pro Pro Thr Lys Tyr Gln Ile Ser Gln Pro Glu
        35                  40                  45

Val Tyr Val Ala Ala Pro Gly Glu Ser Leu Glu Val Arg Cys Leu Leu
    50                  55                  60

Lys Asp Ala Ala Val Ile Ser Trp Thr Lys Asp Gly Val His Leu Gly
65                  70                  75                  80

Pro Asn Asn Arg Thr Val Leu Ile Gly Glu Tyr Leu Gln Ile Lys Gly
                85                  90                  95

Ala Thr Pro Arg Asp Ser Gly Leu Tyr Ala Cys Thr Ala Ser Arg Thr
            100                 105                 110

Val Asp Ser Glu Thr Trp Tyr Phe Met Val Asn Val Thr Asp Ala Ile
        115                 120                 125

Ser Ser Gly Asp Asp Glu Asp Asp Thr Asp Gly Ala Glu Asp Phe Val
    130                 135                 140

Ser Glu Asn Ser Asn Asn Lys Arg Ala Pro Tyr Trp Thr Asn Thr Glu
145                 150                 155                 160

Lys Met Glu Lys Arg Leu His Ala Val Pro Ala Ala Asn Thr Val Lys
                165                 170                 175

Phe Arg Cys Pro Ala Gly Gly Asn Pro Met Pro Thr Met Arg Trp Leu
            180                 185                 190

Lys Asn Gly Lys Glu Phe Lys Gln Glu His Arg Ile Gly Gly Tyr Lys
        195                 200                 205

Val Arg Asn Gln His Trp Ser Leu Ile Met Glu Ser Val Val Pro Ser
    210                 215                 220

Asp Lys Gly Asn Tyr Thr Cys Val Val Glu Asn Glu Tyr Gly Ser Ile
225                 230                 235                 240

Asn His Thr Tyr His Leu Asp Val Val Glu Arg Ser Pro His Arg Pro
                245                 250                 255

Ile Leu Gln Ala Gly Leu Pro Ala Asn Ala Ser Thr Val Val Gly Gly
            260                 265                 270

Asp Val Glu Phe Val Cys Lys Val Tyr Ser Asp Ala Gln Pro His Ile
```

```
                275                 280                 285
Gln Trp Ile Lys His Val Glu Lys Asn Gly Ser Lys Tyr Gly Pro Asp
290                 295                 300

Gly Leu Pro Tyr Leu Lys Val Leu Lys His Ser Gly Ile Asn Ser Ser
305                 310                 315                 320

Asn Ala Glu Val Leu Ala Leu Phe Asn Val Thr Glu Ala Asp Ala Gly
                325                 330                 335

Glu Tyr Ile Cys Lys Val Ser Asn Tyr Ile Gly Gln Ala Asn Gln Ser
                340                 345                 350

Ala Trp Leu Thr Val Leu Pro Lys Gln Gln Ala Pro Gly Arg Glu Lys
                355                 360                 365

Glu Ile Thr Ala Ser Pro Asp Tyr Leu Glu Ile Ala Ile Tyr Cys Ile
                370                 375                 380

Gly Val Phe Leu Ile Ala Cys Met Val Val Thr Val Ile Leu Cys Arg
385                 390                 395                 400

Met Lys Asn Thr Thr Lys Lys Pro Asp Phe Ser Ser Gln Pro Ala Val
                405                 410                 415

His Lys Leu Thr Lys Arg Ile Pro Leu Arg Arg Gln Val Thr Val Ser
                420                 425                 430

Ala Glu Ser Ser Ser Ser Met Asn Ser Asn Thr Pro Leu Val Arg Ile
                435                 440                 445

Thr Thr Arg Leu Ser Ser Thr Ala Asp Thr Pro Met Leu Ala Gly Val
                450                 455                 460

Ser Glu Tyr Glu Leu Pro Glu Asp Pro Lys Trp Glu Phe Pro Arg Asp
465                 470                 475                 480

Lys Leu Thr Leu Gly Lys Pro Leu Gly Glu Gly Cys Phe Gly Gln Val
                485                 490                 495

Val Met Ala Glu Ala Val Gly Ile Asp Lys Asp Lys Pro Lys Glu Ala
                500                 505                 510

Val Thr Val Ala Val Lys Met Leu Lys Asp Asp Ala Thr Glu Lys Asp
                515                 520                 525

Leu Ser Asp Leu Val Ser Glu Met Glu Met Met Lys Met Ile Gly Lys
530                 535                 540

His Lys Asn Ile Ile Asn Leu Leu Gly Ala Cys Thr Gln Asp Gly Pro
545                 550                 555                 560

Leu Tyr Val Ile Val Glu Tyr Ala Ser Lys Gly Asn Leu Arg Glu Tyr
                565                 570                 575

Leu Arg Ala Arg Arg Pro Pro Gly Met Glu Tyr Ser Tyr Asp Ile Asn
                580                 585                 590

Arg Val Pro Glu Glu Gln Met Thr Phe Lys Asp Leu Val Ser Cys Thr
                595                 600                 605

Tyr Gln Leu Ala Arg Gly Met Glu Tyr Leu Ala Ser Gln Lys Cys Ile
                610                 615                 620

His Arg Asp Leu Ala Ala Arg Asn Val Leu Val Thr Glu Asn Asn Val
625                 630                 635                 640

Met Lys Ile Ala Asp Phe Gly Leu Ala Arg Asp Ile Asn Asn Ile Asp
                645                 650                 655

Tyr Tyr Lys Lys Thr Thr Asn Gly Arg Leu Pro Val Lys Trp Met Ala
                660                 665                 670

Pro Glu Ala Leu Phe Asp Arg Val Tyr Thr His Gln Ser Asp Val Trp
                675                 680                 685

Ser Phe Gly Val Leu Met Trp Glu Ile Phe Thr Leu Gly Gly Ser Pro
690                 695                 700
```

```
Tyr Pro Gly Ile Pro Val Glu Glu Leu Phe Lys Leu Leu Lys Glu Gly
705             710                 715                 720

His Arg Met Asp Lys Pro Ala Asn Cys Thr Asn Glu Leu Tyr Met Met
            725                 730                 735

Met Arg Asp Cys Trp His Ala Val Pro Ser Gln Arg Pro Thr Phe Lys
            740                 745                 750

Gln Leu Val Glu Asp Leu Asp Arg Ile Leu Thr Leu Thr Thr Asn Glu
            755                 760                 765

Glu Tyr Leu Asp Leu Ser Gln Pro Leu Glu Gln Tyr Ser Pro Ser Tyr
    770                 775                 780

Pro Asp Thr Arg Ser Ser Cys Ser Ser Gly Asp Asp Ser Val Phe Ser
785             790                 795                 800

Pro Asp Pro Met Pro Tyr Glu Pro Cys Leu Pro Gln Tyr Pro His Ile
            805                 810                 815

Asn Gly Ser Val Lys Thr
            820
```

SUSCEPTIBILITY OF TUMORS TO TYROSINE KINASE INHIBITORS AND TREATMENT THEREOF

CROSS-REFERENCE TO RELATED APPLICATIONS

This application claims the priority of U.S. provisional applications entitled METHODS OF DETERMINING SUSCEPTIBILITY OF TUMORS TO TYROSINE KINASE INHIBITORS, with application No. 61/643,532, filed on May 7, 2012, which is hereby incorporated by reference in its entirety.

FIELD OF THE INVENTION

This invention relates to tyrosine kinases, specifically receptor tyrosine kinases with one or more variants. Further, it relates to methods of using these variants in screens and analyses, including diagnoses, theranoses, and systems for identification susceptibility of tumors to tyrosine inhibitor.

BACKGROUND OF THE INVENTION

Endometrial cancer includes all forms and subtypes of the disease, including for example, serous, mucinous, and endometrioid histological subtypes or any other cancer that starts in the endometrium, which includes the lining of the uterus. Particularly, cancer of the endometrium is the most common gynecologic malignancy and accounts for 6% of all cancers in women. It is estimated there were ~46,000 new cases diagnosed and ~8,000 women dying from this disease in 2011 in the USA. Although early diagnosis largely explains the relatively good overall long-term survival of EC, the 5-year survival rates for women with regional or distant metastatic disease at diagnosis is only ~70% and ~25% respectively. Worse is the outcome for patients with early stage cancers that subsequently recur (5 year survival of ~13%).

Members of the fibroblast growth factor receptor (FGFR) tyrosine kinase family have been shown to be amplified or mutationally activated in endometrial cancer and a variety of other cancer types, including breast cancer, ovarian cancer, lung cancer, gastric cancer, bladder cancer, glioblastoma and rhabdomyosarcoma, making FGFRs an attractive potential therapeutic target. Targeted tyrosine kinase inhibitors (TKIs) have shown success in cancer treatment. However, the long-term efficacy of these TKIs is frequently limited by development of resistance to the TKIs. The resistance developed to TKIs can be due to mutation of the target kinase. It has been shown that shRNA knockdown and kinase inhibition with PD173074 (research only pan-FGFR inhibitor) induced G1 growth arrest and cell death in two FGFR-mutant EC lines (AN3CA and MFE280). Preclinical studies have demonstrated that FGFR inhibition is a viable therapeutic strategy in not only EC, but also a range of malignancies driven by FGFR amplification or mutation, which include breast, endometrial and gastric cancers. However, the remarkable success of small molecule tyrosine kinase inhibitors in the clinic, such as imatinib, has been tempered by the presence of both primary resistance in a subset of patients and the emergence of secondary resistance (acquired resistance) in some, if not all, patients.

Despite the importance of FGFRs as cancer drug targets, little is known about the repertoire of mutations in FGFRs that confer resistance to current FGFR inhibitors. Therefore, there is a need to determine specific resistance profiles for each particular compound by discovering relevant mutation(s) in FGFR. With such a resistance profile, it is possible to identify the drug most likely to benefit patients not only broadly, but also based on their individual spectrum of potential intrinsic resistance, rather than merely the best anti-FGFR agent. Such FGFR mutation(s) can be used to screen for new generations of FGFR inhibitor, whether it is an FGFR-specific inhibitor, or a multi-targeted protein kinase inhibitor, or a combination of selective antagonists, as in an anti-tumor or anti-cancer drug, and subject a patient to a specific treatment that would be responsive.

SUMMARY OF THE INVENTION

One aspect of the present invention provides a method for treating a subject having a cancer with amplified or mutationally activated FGFR2 kinase (fibroblast growth factor receptor). The general method comprises (1) receiving a sample from the subject; (2) analyzing the sample for the presence of at least one FGFR2 kinase mutation variant; wherein the subject is drug resistant to one or more FGFR2 kinase inhibitors if one or more FGFR2 kinase mutation variants selected from the group consisting of M536I, M538I, I548V, N550H, N550K, N550S, V565I, E566G, L618M, E719G, and Y770IfsX14 is present in the sample from the subject; and (3) administering a regimen comprising ponatinib and/or BGJ398 to the subject if at least N550K mutation is present in the patient; or (4) administering a regimen comprising AZD4547 and/or DCC2036 to the subject if at least V565I mutation is present in the subject. The FGFR2 kinase inhibitor in the general method is selected from the group consisting of dovitinib, PD173073, AZD4547, ponatinib, BGJ398, and DCC2036. The sample used in the general method comprises a tumor cell, specifically, a tumor cell dependent on FGFR activity. In one example, the tumor cell is an endometrial cancer cell. The sample may be selected from the group consisting of a biopsy, a tissue, a body fluid, and a single cell, comprising tumor DNA, RNA, protein, peptide or fragments thereof. In the general method, the presence of at least one FGFR2 kinase mutation variant in the sample may be determined by a technique selected from the group consisting of PCR, RT-PCR, sequencing, hybridization, microarray genotyping, HPLC, Mass Spectrometry, and antibody-based immunoassays.

Another aspect of the present invention provides a method for determining drug responsiveness in a subject having cancer with amplified or mutationally activated FGFR2. The method comprises (1) receiving a sample from the subject; (2) analyzing the sample for the presence of at least one FGFR2 kinase mutation variant selected from the group consisting of M536I, M538I, I548V, N550H, N550K, N550S, V565I, E566G, L618M, E719G, and Y770IfsX14; wherein the subject drug resistant to one or more FGFR2 kinase inhibitors if one or more FGFR2 mutation variants is present in the sample from the subject. In one example, the FGFR2 kinase inhibitor is selected from the group consisting of dovitinib, PD173073, AZD4547, ponatinib, BGJ398, and DCC2036. When applying the method, the presence of N550K FGFR2 kinase mutation variant is associated with the drug resistance to dovitinib and AZD4547 in the subject; whereas the presence of N550K FGFR2 kinase mutation variant is associated with the drug sensitivity to ponatinib and/or BGJ398 in the subject; and the presence of V565I FGFR2 kinase mutation variant is associated with the drug sensitivity to AZD4547 and/or DCC2036 in the subject. The sample used in the method is selected from the group consisting of a biopsy, a tissue, a body fluid, and a single cell, which comprises tumor DNA, RNA, protein, peptide or fragments thereof. In applying the method, the presence of at least one FGFR2 kinase mutation variant in the sample is determined by a technique selected from the group consisting of PCR, RT-PCR, sequencing, hybridization, microarray genotyping, HPLC, Mass Spectrometry, and antibody-based immunoassays.

Yet another aspect of this invention provides a combination of markers for identifying and treating a subject having cancer with amplified or mutationally activated FGFR2 kinase, and the marker combination comprises M536I, M538I, I548V, N550H, N550K, N550S, V565I, E566G, L618M, E719G, and Y770IfsX14 FGFR2 kinase mutations. In this marker combination, the presence of one or more of the FGFR2 kinase mutations indicates the cancer with amplified or mutationally activated FGFR2 is resistant to at least one FGFR2 kinase inhibitor. In one example, the FGFR2 kinase inhibitor is selected from the group consisting of dovitinib, PD173073, AZD4547, ponatinib, BGJ398, and DCC2036. Specifically, the presence of N550K FGFR2 kinase mutation variant is associated with drug resistance to dovitinib and AZD4547 in the subject; whereas the presence of N550K FGFR2 kinase mutation variant is associated with the drug sensitivity to ponatinib and/or BGJ398 in the subject, and the presence of V565I FGFR2 kinase mutation variant is associated with the drug sensitivity to AZD4547 and/or DCC2036 in the subject.

Other aspects and iterations of the invention are described in more detail below.

DETAILED DESCRIPTION OF THE INVENTION

Figure 1:
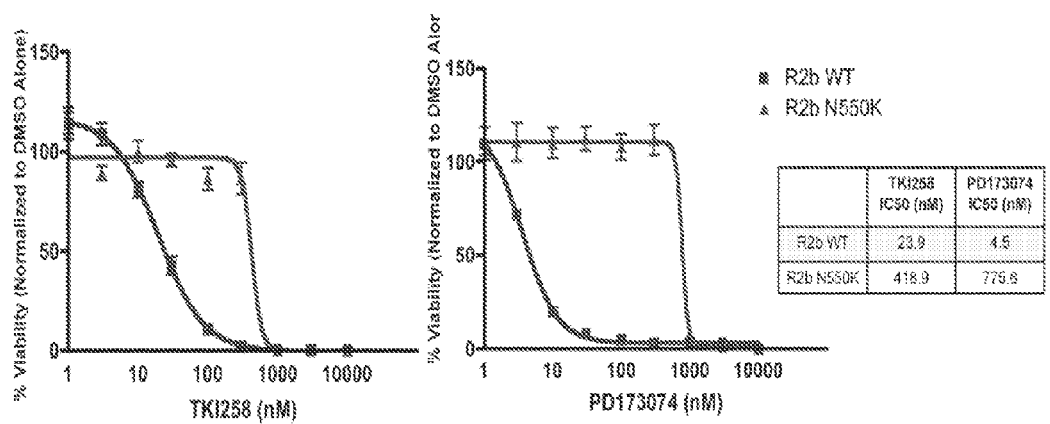
FIG. 1 depicts the $IC_{50}$ graphs of TKI258 and PD173074 in BaF3/FGFR2b wildtype and N550K cells.

The present invention provides a panel of FGFR2 mutation variants, and more specifically, methods and kits for identifying inhibitor susceptible or resistance tumor cells, and a method for screening agents that induce tumor cell death, inhibit tumor growth, or decrease risk of metastasis of a tumor cell, comprising a particular FGFR2 mutation variant disclosed herein.

Receptor tyrosine kinases (RTK)s are the high-affinity cell surface receptors for many polypeptide growth factors, cytokines, and hormones. Of the 90 unique tyrosine kinase genes identified in the human genome, 58 encode receptor tyrosine kinase proteins. There are mainly 5 families of RTKs: epidermal growth factor receptor (EGFR) family; fibroblast growth factor receptor (FGFR) family; vascular endothelial growth factor receptor (VEGFR) family; RET receptor family; and, Eph receptor family. RTKs have been shown not only to be key regulators of normal cellular processes but also to have a critical role in the development and progression of many types of cancer.

I. Fibroblast Growth Gactor Receptors (FGFRs)

Fibroblast growth factors (FGFs) acting through their cognate receptors (FGFRs) play vital roles in development and de-regulation of FGF/FGFR signaling is associated with many developmental syndromes. FGF/FGFR signaling is important in tumor angiogenesis and FGFRs drive oncogenes in certain cancers and act in a cell autonomous fashion to maintain the malignant properties of tumor cells. Members of the fibroblast growth factor receptor (FGFR) tyrosine kinase family have been shown to be amplified or mutationally activated in a variety of cancer types, including breast, endometrial, ovarian, lung, gastric, and bladder cancers, as well as glioblastoma and rhabdomyosarcoma, making FGFRs an attractive potential therapeutic target.

The FGFRs consist of an extracellular ligand domain composed of three immunoglobulin-like domains, a single transmembrane helix domain, and an intracellular domain with tyrosine kinase activity. The natural alternate splicing of four FGFR genes, FGFR1, FGFR2, FGFR3, and FGFR4, results in the production of over 48 different isoforms of FGFR, with FGFR2b being one of them. FGFR isoforms vary in their extracellular region and ligand-binding properties but all share a common and kinase domains.

It has been observed that the activation of wild-type (WT) FGFR, or the subsequent acquisition of activating mutations of FGFR is associated with cancer progression, and impacts drug response and/or resistance, chemotherapy response and/or resistance, and survival rate.

A. FGFR2

The concept of the FGFR2 gene encompasses a gene of human origin with a coding nucleotide sequence set forth in SEQ ID NO:1, or homologs including allelic variants and orthologs. The FGFR2 protein encompasses a protein, also preferably of human origin, having the amino acid sequence set forth in SEQ ID NO:2 or homologs, including orthologs thereof.

FGFR2 belongs to a family of structurally related tyrosine kinase receptors (FGFRs 1-4) encoded by four different genes. FGFR2 is a glycoprotein composed of three extracellular immunoglobulin-like (Ig) domains, a transmembrane domain, and a split tyrosine kinase domain. Alternative splicing in the IgIII domain is a primary determinant of both the patterns of redundancy and specificity in FGF/FGFR binding and signaling. This splicing event is tissue specific and gives rise to the IIIb and Mc receptor isoforms for FGFR1 and FGFR3, which possess distinct ligand specificities. For FGFR2, cells of an epithelial linage only express the "IIIb" isoform encoded by exon 8 (FGFR2b; SEQ ID NO:2; NP_075259.2), while mesenchymally derived cells exclusively express the "IIIc" isoform utilizing exon 9 (FGFR2c; SEQ ID NO:3; NP_000132.1). The FGFR2b isoform predominantly binds FGF1, FGF3, FGF7 and FGF10, while FGFR2c does not bind FGF7 and FGF10 but does bind FGF1, FGF2, FGF4, FGF6, and FGF8 with high affinity.

A mutation in FGFR2 that causes increased activity of FGFR2 in a test subject or a biological sample may also be called an activation mutation. Activation mutations display higher total FGFR2 activity in the test subject or biological sample in comparison with a control, e.g., a healthy subject or a standard sample. Therefore, the activity of FGFR2 in a healthy subject or a standard sample is 5%, 10%, 20%, 30%, 40%, 50%, 60%, 70%, 80%, 90%, 95%, 99% relative to that in a subject or a sample carrying activation mutation in FGFR2. The increased activity of FGFR2 in a subject or a sample carrying activation mutation may result from, for example, increased basal FGFR2 activity, prolonged stimulation, delayed degradation, or over-expression, e.g., due to enhanced ligand binding, promiscuous or inappropriate ligand binding, constitutive receptor dimerization, impaired recycling resulting in augmentation of signaling, delayed degradation, or kinase activation.

A higher expression level of FGFR2 may result from, for example, a mutation in a non-coding region of a FGFR2 gene or a mutation in a coding or non-coding gene involved in FGFR2 transcription or translation. The expression level of FGFR2 can be determined, for example, by comparing FGFR2 mRNA or the level of FGFR2 protein in a test subject as compared to a control, for example, by comparing the tumor to normal endometrium (e.g., a normal adjacent endometrium sample).

Conserved variants encompass any mutation or other variant in which a given amino acid residue in a protein or enzyme has been changed without altering the overall conformation and function of the polypeptide, including, but not limited to, replacement of an amino acid with one having similar properties (such as, for example, polarity, hydrogen bonding potential, acidic, basic, hydrophobic, aromatic, and the like). Amino acids with similar properties are well known in the art. For example, arginine, histidine and lysine are hydrophilic-basic amino acids and may be interchangeable. Similarly, isoleucine, a hydrophobic amino acid, may be replaced with leucine, methionine or valine. Depending on the location of the mutation in the overall context of the protein, some substitution may have little or no effect on the apparent molecular weight or isoelectric point of the protein or polypeptide. However some conserved variants have been found to alter protein conformation and function, including several variants discovered and disclosed herein.

Amino acids other than those indicated as conserved may differ in a protein or enzyme so that the percent protein or amino acid sequence similarity between any two proteins of similar function may vary and may be, for example, from 70% to 99% as determined according to an alignment scheme such as by the Cluster Method, wherein similarity is based on the MEGALIGN algorithm. The concept of a variant further encompasses a polypeptide or enzyme which has at least 60%, 75%, 85%, 90%, or 95%, amino acid identity as determined by algorithms such as BLAST or FASTA and which has the same or substantially similar properties and/or activities as the native or parent protein or enzyme to which it is compared.

One example of such a variant is a gain-of-function variant. Gain-of-function variants of polypeptides encompass any variant in which a change in one or more amino acid residues in a protein or enzyme improves the activity of the polypeptide. Examples of activities of a polypeptide that may be improved by a change resulting in a gain of function variant include but are not limited to enzymatic activity, binding affinity, phosphorylation or dephosphorylation efficiency, activation, deactivation, or any other activity or property of a protein that may be quantitatively measured by some method now known or yet to be disclosed.

Proteins that possess a common evolutionary origin may be homologous or similar to one another. Examples of homologous or similar proteins include proteins from superfamilies (e.g., the immunoglobulin superfamily) and homologous proteins from different species. Such proteins and their encoding genes have sequence homology with one another. The homology may be expressed in terms of percent similarity or the presence of specific residues or motifs at conserved positions.

A mutation may be any detectable change in genetic material such as DNA, or a corresponding change in the RNA or protein product of that genetic material. A mutant may be any biological material in which one or more mutations are detected when compared to a control material. Examples of mutations include gene mutations, in which the DNA sequence of a gene or any controlling elements surrounding the gene is altered. Controlling elements include promoter, enhancer, suppressor or silencing elements capable of controlling a given gene. Other examples of mutations include alterations in the products of DNA expression such as RNA or protein that result from corresponding mutations in the DNA. Mutants may also be interchangeably called variants. The concept of a mutant includes any change in DNA sequence specific to the tumor cell (not present in DNA prepared from normal, non-neoplastic tissues).

B. FGFR Inhibitors and Mutations Leading to Inhibitor Resistance

A number of FGFR inhibitors are currently progressing through clinical trials. Preclinical in vitro and in vivo studies have indicated that FGFR kinase inhibition in FGFR dependent tumors is a rational approach to target these cancers. While more selective anti-FGFR inhibitors are entering early clinical development, the most clinically advanced inhibitors are multi-kinase inhibitors, often developed as antiangiogenic agents. Dovitinib is the multi-kinase inhibitor that has shown the most promising results in multiple FGFR-dependent cancers. Dovitinib (TKI258, previously CHIR258) is an ATP-competitive tyrosine kinase inhibitor with activity against FGFR1-4, VEGFR1-3, PDGFRB, c-KIT, CSF1R and FLT3. It has shown preclinical anti-tumor activity in a range of different cancers including cancer models characterized by FGFR activation such as multiple myeloma, acute myelogenous leukemia, prostate, bladder and gastric cancer. Dovitinib has demonstrated anti-tumor activity in several phase I clinical trials with partial responses (PRs) and stable disease (SD) observed in several patients. Dovitinib is currently in phase II clinical trials in renal cell carcinoma patients as an anti-angiogenic agent as well as in several malignancies associated with FGFR activation e.g. multiple myeloma with t(4; 14) translocation (activated FGFR3) (Clinical Trials identifier: NCT01058434), and advanced urothelial carcinomas with and without mutations in FGFR3 (NCT00790426). It is also in a clinical phase II study in patients with advanced endometrial cancers expressing wild-type or mutant FGFR2 (NCT01379534).

Despite the initial clinical effectiveness of kinase inhibitors, the long-term efficacy of these agents is hampered by intrinsic resistance in a subset of patients and the development of acquired resistance in a proportion of responders. One resistance mechanism common to many kinase inhibitors is the acquisition of secondary mutations in the kinase domain. Mutations of the gatekeeper residue of the target kinase are the most frequently detected drug resistant mutation in the clinic. Notably, mutation of the gatekeeper residue in Bcr-Abl (T315I) is detected with high frequency in chronic myelogenous leukemia (CML) patients with resistance against imatinib. Likewise, mutation of the gatekeeper residue (T790M) in the epidermal growth factor receptor (EGFR) occurs in ~50% of tumors with acquired erlotinib or gefitinib resistance and represents a major obstacle for treatment success with targeted EGFR inhibitors. Substitutions of gatekeeper residues with larger hydrophobic residues have been shown to sterically interfere with access of drug to the hydrophobic pocket in the ATP binding cleft. Bcr-Abl inhibitors have also been shown to form critical hydrogen bonds with the side chain hydroxyl group of T315. Moreover, the gatekeeper mutations appear to enhance tyrosine kinase activity by stabilizing a hydrophobic spine, a network of hydrophobic interactions characteristic of activated kinases. In CML, the realization that patients acquire resistance after initial response led to the development of more potent second generation inhibitors such as nilotinib and dasatinib; however like imatinib, these inhibitors do not have activity against the T315I gatekeeper mutation. This led to the structure-based design of ponatinib (AP24534), a third generation inhibitor designed to have activity against wild-type Bcr-Abl as well as Bcr-Abl-T315I.

TKI258 (dovitinib), a multitargeted receptor tyrosine kinase inhibitor has been shown to have considerable preclinical activity in cancer models with FGFR activation.

Targeted tyrosine kinase inhibitors (TKIs) have demonstrated dramatic clinical responses in the subset of patients whose tumors are 'addicted' to the oncogenic activity of the target kinase. However, the long-term efficacy of these agents is frequently limited by development of resistance to the targeted agent, often due to mutation of the target kinase or activation of alternative downstream or parallel signaling pathways. Identifying the mechanisms of resistance to targeted agents can aid the development of second-generation inhibitors and provide a mechanistic basis of combination with other molecularly targeted agents.

Resistance to TKIs often results from mutations within amino acid sequences that encode important structural features of the kinase. The kinase gatekeeper residue, which controls access to a hydrophobic pocket of the enzymatic active site, has been suggested to be a conserved hotspot of resistance formation. The most frequent site of clinically-detected drug resistant mutations is the gatekeeper residue of the target kinase (Table A). Mutation of the gatekeeper residue in FGFR1 to V561M results in resistance to the broadly active tyrosine kinase inhibitor PP58, suggesting mutation of this gatekeeper residue may function as a common mechanism of resistance to FGFR inhibitors.

TABLE A

Gatekeeper residues whose mutation has been clinically detected and associated with resistance to kinase inhibitors.

| Kinase | Gatekeeper Residue | | | | | Drug-Resistant Gatekeeper Mutations | Tyrosine Kinase Inhibitor |
|---|---|---|---|---|---|---|---|
| C-KIT | V | I | T670 | E | Y | T670I | imatinib |
| c-ABL | I | I | T315 | E | F | T315I | Imatinib, dasatinib |
| PDGFRA | I | I | T674 | E | Y | T674I | imatinib |
| EGFR | L | I | T790 | Q | L | T790M | gefitinib, erlotinib |
| FGFR1 | V | I | V561 | E | Y | na | |
| FGFR2b | V | I | V565 | E | Y | na | |

II. Methods of Identifying Candidates for Treatment with FGFR2 Inhibitors

A. Subject and Sample

A subject includes any human or non-human mammal, including for example: a primate, cow, horse, pig, sheep, goat, dog, cat, or rodent, capable of developing endometrial cancer including human patients that are suspected of having endometrial cancer, that have been diagnosed with endometrial cancer, or that have a family history of endometrial cancer. Methods of identifying subjects suspected of having endometrial cancer include but are not limited to: physical examination, family medical history, subject medical history, endometrial biopsy, or a number of imaging technologies such as ultrasonography, computed tomography, magnetic resonance imaging, magnetic resonance spectroscopy, or positron emission tomography. Methods of diagnosing endometrial cancer as well as the staging, grading, or other clinical delineation of endometrial cancer are well known to those of skill in the medical arts.

A sample may be a body fluid, such as serum, plasma, whole blood, urine, mucus, gastric juices, pancreatic juices, or lymph, from which free floating DNA, RNA, protein, peptide or fragments thereof may be detected and associated to tumor related mutations. Alternatively, a sample may be any cell source from which DNA, including genomic, somatic, and germline DNA may be obtained. In endometrial cancer, a biological sample is often obtained from the uterus and generally includes one or more endometrial tumor cells. Tumor cells may be obtained by any method now known in the art or yet to be disclosed, including for example, surgical resection, laser capture microdissection, isolation from blood or other fluids including lavage fluid, or any other method capable of obtaining and, if necessary, concentrating endometrial tumor cells.

The cell in a sample may be a tumor cell or a cancer cell for which growth may be slowed by the disclosed combination of pharmaceutical compositions either alone or in combination with another treatment modality, includes solid tumors such as fibrosarcoma, myxosarcoma, liposarcoma, chondrosarcoma, osteogenic sarcoma, chordoma, angiosarcoma, endothelio sarcoma, lymphangiosarcoma, lymphangioendothelio sarcoma, synovioma, mesothelioma, Ewing's tumor, leiomyosarcoma, rhabdomyosarcoma, colon cancer, colorectal cancer, kidney cancer, pancreatic cancer, bone cancer, breast cancer, ovarian cancer, prostate cancer, esophageal cancer, stomach cancer, oral cancer, nasal cancer, throat cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, uterine cancer, testicular cancer, small cell lung carcinoma, bladder carcinoma, lung cancer, epithelial carcinoma, glioma, glioblastoma multiforme, astrocytoma, medulloblastoma, craniopharyngioma, ependymoma, pinealoma, hemangioblastoma, acoustic neuroma, oligodendroglioma, meningioma, skin cancer, melanoma, neuroblastoma, and retinoblastoma.

Additional cancers for which growth may be slowed by the disclosed combination of pharmaceutical compositions include blood borne cancers such as acute lymphoblastic leukemia ("ALL,"), acute lymphoblastic B-cell leukemia, acute lymphoblastic T-cell leukemia, acute myeloblastic leukemia ("AML"), acute promyelocytic leukemia ("APL"), acute monoblastic leukemia, acute erythroleukemic leukemia, acute megakaryoblastic leukemia, acute myelomonocytic leukemia, acute nonlymphocyctic leukemia, acute undifferentiated leukemia, chronic myelocytic leukemia ("CML"), chronic lymphocytic leukemia ("CLL"), hairy cell leukemia, multiple myeloma, lymphoblastic leukemia, myelogenous leukemia, lymphocytic leukemia, myelocytic leukemia, Hodgkin's disease, non-Hodgkin's Lymphoma, Waldenstrom's macroglobulinemia, Heavy chain disease, and Polycythemia vera B. Detection of FGFR2 Variants The presence of FGFR2 gene mutations in endometrial cancer strongly suggests that other human cancers may have similar mutations. When present in a cancer, mutant isoforms of FGFR2 represent a therapeutic target for tyrosine kinase inhibitors (TKIs), immunotherapy, and other novel targeted approaches, particularly to decrease risk of tumor metastasis. In cases where the resistance resulted from a FGFR2 mutation is incomplete, such that patients carrying such a mutation would respond to a higher dose of drug, the mutations variant of FGFR2 may be used to identify "high-dose responders." The selection of patients for therapy targeting variant FGFR2 isoforms to induce cancer cell death, reduce cancer growth, or decrease risk of metastasis would be optimized by pre-therapy analysis of cancer cells for the presence of FGFR2 gene mutations.

Analysis based on the presence of a FGFR2 variant can also be a type of test, assay, examination, result, readout, or interpretation that correlates with an increased or decreased probability that an individual has had, currently has, or will develop a particular disease, disorder, symptom, syndrome, or any condition related to health or bodily state. Examples of disease outcomes include, but need not be limited to, survival, death, progression of existing disease, remission of existing disease, initiation or onset of a disease in an otherwise disease-free subject, or the continued lack of disease in a subject in which there has been a remission of disease. Assessing the risk of a disease outcome also encompasses the concept of prognosis. A prognosis may be any assessment of the risk of disease outcome in an individual in which a particular disease has been diagnosed.

Alternatively, predicting a subject's response to a therapy, such as a drug therapy, based on the presence of a FGFR2 variant encompasses the concept of theranosis. Theranostic methods encompass detecting a mutation in the FGFR2 protein including mutations that result in increased activity of the FGFR2 protein. Examples of such mutations include mutations occurring in the junction between the immunoglobulin-like (Ig) domains II and III; mutations occurring in the IgIII domain; mutations occurring in the junction between the IgIII domain and the transmembrane (TM) domain; mutations occurring in the TM domain; mutations occurring in the junction between the TM domain and the tyrosine kinase domain I; mutations occurring in the tyrosine kinase domain I, or mutations occurring in the tyrosine kinase domain II. Such mutations may induce an amino acid substitution. Examples of such amino acid substitutions induced by mutations include but are not limited to: an S to W mutation at position 252, a P to R mutation at position 253, an S to C mutation at position 373, a Y to C mutation at position 376, a C to R mutation at position 383, an M to R mutation at position 392, a V to D mutation at position 396, an L to M mutation at position 398, an I to V mutation at position 548, an N to K mutation at position 550, an N to H mutation at position 550, and a K to E mutation at position 660 with position numbers as indicated in SEQ ID NO. 2. In one nonlimiting embodiment, the mutation consists of a deletion of nucleotide C and T at position 2290-91 of the nucleotide sequence (NM-02297.2) or an IVS10+2A>C splicing mutation with position numbers as indicated in SEQ ID. NO. 1 or any other somatic mutation found in an endometrial tumor cell.

Detection of FGFR2 variants can be based on PCR-based assays for these mutations, using for instance one or more of the following approaches: size fractionation by gel electrophoresis, direct sequencing, single-strand conformation polymorphism (SSCP), high pressure liquid chromatography (including partially denaturing HPLC), allele-specific hybridization, amplification refractory mutation screening, FGFR2 mutation screening by oligonucleotide microarray, restriction fragment polymorphism, MALDI-TOF mass spectrometry, or various related technologies (Grompe, Nature Genetics, 5: 111-117, 1993; Perlin & Szabady, Hum. Mutat., 19: 361-373, 2002; Amos & and Patnaik, Hum. Mutat., 19: 324-333, 2002; Cotton, Hum. Mutat., 19: 313-314, 2002; Stirewalt et al., Blood, 97: 3589-3595, 2001; Hung et al., Blood Coagul. Fibrinolysis, 13: 117-122, 2002; Larsen et al., Pharmacogenomics, 2: 387-399, 2001; Shchepinov et al., Nucleic Acids Res., 29: 3864-3872, 2001).

Mutated forms of FGFR2 nucleic acids, such as in FGFR2 DNA or any transcripts (including any splice variants now known or yet to be disclosed) as well as a deregulated expression (including overexpression or underexpression) of FGFR2 or other elements of a FGFR2 pathway may be detected by any of a variety of suitable methods.

Any method capable of detecting a mutated nucleic acid in a biological sample now known or yet to be disclosed may be employed and many strategies of genotypic analysis are now known to those skilled in the art. Some of these methods use nucleic acid sequences such as specific oligonucleotides to detect mutations in an FGFR2 nucleic acid in a biological sample. Such oligonucleotides may specifically hybridize to a nucleic acid sequence containing the specific mutation, or to a region adjacent to the site of mutation. Other methods use primers that permit amplification of all or part of an FGFR2 nucleic acid. Alternatively, or in combination with such techniques, oligonucleotide sequencing described herein or known to the skilled artisan may be applied to detect the FGFR2 mutations. One skilled in the art may use hybridization probes in solution and in embodiments employing solid-phase procedures. In such procedures, the test nucleic acid is adsorbed or otherwise affixed to a selected matrix or surface. The fixed, single-stranded nucleic acid is then subjected to specific hybridization with selected probes. Alternatively, one skilled in the art may use oligonucleotide primers in an amplification technique, such as PCR or reverse-PCR ("reverse polymerase chain reaction"), to specifically amplify a target DNA or mRNA, respectively. Such primers include primers that permit amplification of FGFR2 exons.

One example of such a method includes but is not limited to the following: contacting a biological sample containing DNA with specific oligonucleotides permitting the amplification of all or part of the FGFR2 gene, the DNA contained in the sample having been rendered accessible, where appropriate, to hybridization, and under conditions permitting a hybridization of the primers with the DNA contained in the biological sample; amplifying said DNA; detecting the amplification products; and comparing the amplified products obtained to the amplified products obtained with a normal control biological sample, and thereby detecting an abnormality in the FGFR2 gene if such abnormality is present and not detecting an abnormality if such abnormality is not present.

Alternatively, a sample may be sequenced directly with no amplification. In such methods, the sequenced DNA is compared to a normal genomic control sequence. The control sequence may be obtained from another subject or from a noncancerous sample from the same subject. One such method of sequencing is allele specific primer extension in which sample DNA hybridized to a chip is used as a synthesis template with the affixed oligonucleotide as a primer. Only the added dNTP's are labeled. Incorporation of the labeled dNTP then serves as a signal indicating the presence of the mutation. The fluorescent label may be detected by any of a number of instruments configured to read at least four different fluorescent labels on a DNA chip. In an alternative method, the identity of the final dNTP added to the oligonucleotide may be assessed by mass spectrometry. In this method, the dNTP's may, but need not, be labeled with a label of known molecular weight.

Other methods of detecting abnormalities in FGFR2 include those that detect abnormalities in the transcript of the FGFR2 gene. Such methods include amplifying mRNA transcripts in a biological sample by techniques such as RT-PCR (reverse transcription PCR). One example of such a method includes but is not limited to the following: producing cDNA from mRNA contained in a biological sample; contacting said cDNA with specific oligonucleotides capable of amplifying of all or part of the transcript of the FGFR2 gene, under conditions capable of hybridizing the primers with said cDNA; amplifying said cDNA; detecting the amplification products; comparing the amplified products obtained to the amplified products obtained with a normal control biological sample, and thereby detecting an abnormality in the transcript of the FGFR2 gene if such an abnormality is present and not detecting an abnormality if such an abnormality is not present. A control may be any noncancerous endometrial tissue control sample known as noncancerous to those skilled in the art, for example, a normal adjacent endometrium sample or a normal FGFR2 mRNA or DNA, obtained from blood, buccal swab or other source.

Additionally, RT-PCR allows visualization of the consequences of a splicing mutation such as exon skipping or aberrant splicing due to the activation of a cryptic site.

Nucleic acids that hybridize to mutant forms of FGFR2 may be used as probes in theranostic assays. Such a probe may comprise a substantially purified oligonucleotide that further includes a region having a nucleotide sequence that is capable of hybridizing specifically to a region of a FGFR2 gene that may be mutant or polymorphic. Such probes can then be used to detect specifically which, if any, mutation of the FGFR2 gene is present in a sample taken from a subject. The mutant or polymorphic region can be located in the promoter, exon, or intron sequences of the FGFR2 gene. In general, such probes have a sufficient number of nucleotides to allow specific hybridization to the target nucleotide sequence. Probes complementary to mutant sequences with the appropriate specificity may be constructed by those skilled in the art. For example, a portion of the FGFR2 gene may first be amplified and isolated from chromosomal DNA and hybridized to a probe. In such a case a probe of 10, 15, 20, 30, 50, or 100 nucleotides may be used.

The probe or primer may include a label. A label may be any substance capable of aiding a machine, detector, sensor, device, or enhanced or unenhanced human eye from differentiating a sequence that contains a particular allele from a sequence that does not contain the allele. Examples of labels include but are not limited to: a radioactive isotope or chelate thereof, a dye (fluorescent or nonfluorescent) stain, enzyme, or nonradioactive metal. Specific examples include but are not limited to: fluorescein, biotin, digoxigenin, alkaline phosphatase, biotin, streptavidin, $^3$H, $^{14}$C, $^{32}$P, $^{35}$S, or any other compound capable of emitting radiation, rhodamine, 4-(4'-dimethylamino-phenylazo)benzoic acid ("Dabcyl"); 4-(4'-dimethylamino-phenylazo)sulfonic acid (sulfonyl chloride) ("Dabsyl"); 5-((2-aminoethyl)-amino)-naphtalene-1-sulfonic acid ("EDANS"); Psoralene derivatives, haptens, cyanines, acridines, fluorescent rhodol derivatives, cholesterol derivatives; ethylenediaminetetraaceticacid ("EDTA") and derivatives thereof or any other compound that signals the presence of bound ligand to an allele. In one embodiment of the invention, the label includes one or more dyes optimized for use in genotyping. Examples of such dyes include but are not limited to: dR110, 5-FAM, 6FAM, dR6G, JOE, HEX, VIC, TET, dTAMRA, TAMRA, NED, dROX, PET, and LIZ.

Alternatively, the probe may be modified to be more stable. Exemplary nucleic acid molecules that may be used to modify the probe to increase stability include phosphoramidate, phosphothioate and methylphosphonate analogs of DNA (see also, U.S. Pat. Nos. 5,176,996; 5,264,564; and 5,256,775).

One may use HPLC or denaturing HPLC (DHPLC) techniques to analyze the FGFR2 nucleic acids. DHPLC was developed when observing that, when HPLC analyses are carried out at a partially denaturing temperature, homoduplexes can be separated from heteroduplexes having the same base pair length (Hayward-Lester, et al., Genome Research, 1995, 5:494; Underhill, et al., Proc. Natl. Acad. Sci. USA, 1996, 93:193; Doris, et al., DHPLC Workshop, 1997, Stanford University). Thus, the use of DHPLC was applied to mutation detection (Underhill, et al., Genome Research, 1997, 7:996; Liu, et al., Nucleic Acid Res., 1998, 26; 1396). DHPLC can separate heteroduplexes that differ by as little as one base pair. "Matched Ion Polynucleotide Chromatography" (MIPC), or Denaturing "Matched Ion Polynucleotide Chromatography" (DMIPC) as described in U.S. Pat. No. 6,287,822 or 6,024,878, are additional separation methods.

Alternatively, one can use the DGGE method (Denaturing Gradient Gel Electrophoresis), or the SSCP method (Single Strand Conformation Polymorphism) for detecting an abnormality in the FGFR2 gene. DGGE is a method for resolving multiple DNA fragments of identical length on the basis of sequence differences as small as a single base pair change, using electrophoresis through a gel containing varying concentrations of denaturant (Guldberg et al., Nuc. Acids Res. 1994, 22:880). SSCP is a method for detecting sequence differences between two DNAs, comprising hybridization of the two species with subsequent mismatch detection by gel electrophoresis (Ravnik-Glavac et al., Hum. Mol. Genet. 1994, 3:801). "HOT cleavage", a method for detecting sequence differences between two DNAs, comprising hybridization of the two species with subsequent mismatch detection by chemical cleavage (Cotton, et al, Proc. Natl. Acad. Sci. USA 1988, 85:4397), can also be used.

Techniques using microarrays including microarrays that utilize high-throughput screening, may also be advantageously implemented to detect genetic abnormalities or assess gene expression. Gene expression may be that of the FGFR2 gene or the expression of another gene upstream or downstream in a pathway of which FGFR2 is a component or any other gene the expression of which correlates with FGFR2 expression. Microarrays may be designed so that the same set of identical oligonucleotides is attached to at least two selected discrete regions of the array, so that one can easily compare a normal sample, contacted with one of said selected regions of the array, against a test sample, contacted with another of said selected regions. These arrays use microfluidic conduits to avoid the mixture of normal sample and test sample. Examples of microarray techniques include those developed by Nanogen, Inc. (San Diego, Calif.) and those developed by Affymetrix (Santa Clara, Calif.). However, all types of microarrays, also called "gene chips" or "DNA chips", may be adapted for the identification of mutations. Such microarrays are well known in the art.

The solid support on which oligonucleotides are attached may be made from glass, silicon, plastic (e.g., polypropylene, nylon), polyacrylamide, nitrocellulose, or other materials now known or yet to be disclosed. One method for attaching the nucleic acids to a surface is by printing on glass plates, as is described generally by Schena et al., Science 1995, 270: 467-470. This method is especially useful for preparing microarrays of cDNA. See also, DeRisi et al., Nature Genetics 1996, 14:457-460; Shalon et al., Genome Res. 1996, 6:639645; and Schena et al., Proc. Natl. Acad. Sci. USA 1995, 93:10539-11286.

Other methods for making microarrays, e.g., by masking (Maskos and Southern, Nuc. Acids Res. 1992, 20:1679-1684), may also be used. In principal, any type of array, for example, dot blots on a nylon hybridization membrane (see Sambrook et al., Molecular Cloning A Laboratory Manual (2nd Ed.), Vol. 1-3, Cold Spring Harbor Laboratory, Cold Spring Harbor, N.Y., 1989) could be used, although, as will be recognized by those of skill in the art. For these assays nucleic acid hybridization and wash conditions are chosen so that the attached oligonucleotides specifically hybridize to at least a portion of the FGFR2 gene present in the tested sample sequence but does not hybridize to a site with a non-complementary nucleic acid sequence. The terms "hybridize" and "bind" are used interchangeably.

Alternatively, one may use allele specific hybridization to detect the mutant. In allele-specific hybridization, oligonucleotide sequences representing all possible variations at a polymorphic site are included on a DNA chip. The chip and sample are subject to conditions under which the labeled sample DNA will only bind to an oligonucleotide with an exact sequence match. In allele-specific primer extension, sample DNA hybridized to the chip may be used as a synthesis template with the affixed oligonucleotide as a primer. Under this method, only the added dNTP's are labeled. Incorporation of the labeled dNTP then serves as the signal indicating the presence of the allele. The fluorescent label may be detected by any of a number of instruments configured to read at least four different fluorescent labels on a DNA chip. In another alternative, the identity of the final dNTP added to the oligonucleotide may be assessed by mass spectrometry. In this alternative, the dNTP's may, but need not be labeled with a label of known molecular weight.

One polynucleotide sequence is considered complementary to another when, if the shorter of the polynucleotides is less than or equal to 25 bases, there are no mismatches using standard base-pairing rules or, if the shorter of the polynucleotides is longer than 25 bases, there is no more than a 5% mismatch. Preferably, the polynucleotides are perfectly complementary (no mismatches). It can easily be demonstrated that specific hybridization conditions result in specific hybridization by carrying out a hybridization assay including negative controls (see, e.g., Shalon et al, supra, and Chee et al., Science 1996, 274:610-614).

A variety of methods are available for detection and analysis of the hybridization events. Depending on the label used, detection and analysis may be carried out, for example fluorimetrically, colorimetrically or by autoradiography. By observing and measuring emitted radiation, such as fluorescent radiation or a particle emission, information may be obtained about the hybridization events. When fluorescently labeled probes are used, the fluorescence emissions at each site of transcript array can be detected by, for example, scanning confocal laser microscopy. In scanning confocal laser microscopy, a separate scan using the appropriate excitation line, is carried out for each of at least two fluorophores used to label probes. Alternatively, a laser that allows simultaneous specimen illumination at wavelengths specific to the two fluorophores and emissions from the two fluorophores may be used (see Shalon et al. Genome Res. 1996, 6:639-695).

In addition, mutant or variant FGFR2 proteins may be detected through novel epitopes recognized by polyclonal and/or monoclonal antibodies used in ELISA, immunoblotting, flow cytometric, immunohistochemical and other mutant protein detection strategies (Wong et al., Cancer Res., 46: 6029-6033, 1986; Luwor et al., Cancer Res., 61: 5355-5361, 2001; Mishima et al., Cancer Res., 61: 5349-5354, 2001; Ijaz et al., J. Med. Virol., 63: 210-216, 2001). In ELISA assays, an antibody raised against whole FGFR2, or a fragment of FGFR2, or any mutant form of FGFR2 is immobilized onto a solid surface capable of binding proteins nonspecifically. Alternatively, purified FGFR2 or FGFR2 mutant, or any fragment thereof is immobilized onto the solid surface directly. Antibodies to be used in immunoassays that detect the presence of mutant forms of FGFR2 may be produced by any of a number of techniques that include, but are not limited to, the techniques below. Such antibodies include, but are not limited to, polyclonal, monoclonal, chimeric, single chain, Fab fragments, Fab expression library, humanized antibodies, or any functional fragments thereof.

Quantification of FGFR2 in the sample may then be achieved by measuring the degree of color generation using, for example, a visible spectra spectrophotometer. Examples of the enzyme to which the second antibody is conjugated include but are not limited to peroxidase and alkaline phosphatase. Examples of the substrate include a peroxidase substrate such as tetramethylbenzidine or any other substrate that changes the color or another property of a solution in response to the presence of a particular enzyme. The test protein concentration may be determined by comparison with a standard curve. These protocols are detailed in Current Protocols in Molecular Biology, V. 2 Ch. 11 and Antibodies, a Laboratory Manual, Ed Harlow, David Lane, Cold Spring Harbor Laboratory (1988) pp 579-593.

Other examples of immunoassays that may be used to detect mutant forms of FGFR2 protein include radioimmunoassay, sandwich immunoassays, immunoradiometric assays, gel diffusion precipitin reactions, immunodiffusion asays, in situ immuoassays or immunohistochemistry assays (IHC), precipitation reactions, agglutination assays, complement fixation assays, immunofluorescence assays, protein A assays, immunoelectrophoresis assays, flow cytometry based assays or any other technique now known or yet to be developed that utilizes a specific antibody to detect mutant FGFR2.

Additionally variant FGFR2 proteins could be detected by mass spectrometry assays coupled to immunaffinity assays, the use of matrix-assisted laser desorption/ionization time-of-flight (MALDI-TOF) mass mapping and liquid chromatography/quadrupole time-of-flight electrospray ionization tandem mass spectrometry (LC/Q-TOF-ESI-MS/MS) sequence tag of tumor derived proteins separated by two-dimensional polyacrylamide gel electrophoresis (2D-PAGE) (Kiernan et al., Anal. Biochem., 301: 49-56, 2002; Poutanen et al., Mass Spectrom., 15: 1685-1692, 2001). All of these approaches may be used to detect a sequence anomaly or variant of the FGFR2 protein, a relative increase in the phosphorylation of the protein, or an increase in the inherent kinase activity of the protein.

C. Detection of Altered FGFR Activation

In addition to direct detection of variant FGFR2 proteins, it is expected that various FGFR2 variants will result in distinctive signal transduction profiles that could be detected by global gene expression profile or analysis of the activation or phosphorylation of various signaling intermediates (e.g., Stat3, Akt, ERK1/2, or S6K). For example, a FGFR2 receptor activation mutation may increase activation of the receptor by enhancing ligand binding, promoting altered or promiscuous ligand affinity with reduced selectivity, constitutive receptor dimerization, delayed degradation, impaired recycling from the cell membrane, overexpression, or kinase activation.

In one embodiment of the invention, the activity level of the FGFR2 variant protein in an endometrial cancer cell of a test subject may be assessed and compared to the activity in endometrial cells of a control subject. The increased activity of FGFR2 variant protein in the test subject compared to the control subject is indicative of drug resistance. The level of FGFR2 activity may be assessed by determining the level of activity in a FGFR2 signaling pathway through any method now known or yet to be developed. Examples include, but need not be limited to, assessing the expression of targets up- or down-regulated upon FGFR2 signaling, assessing the phosphorylation status of proteins phosphorylated or dephosphorylated on FGFR2 signaling, or any other method capable of detecting an increase in FGFR2 activity or ligand promiscuity.

It is believed that the nature and location of FGFR mutations affects the sensitivity of the resultant mutant protein to various TKIs. In some examples, a TKI may selectively inhibit wildtype FGFR2 protein, such that the TKI inhibits tyrosine kinase activity of a wildtype FGFR2 protein to a greater extent than it inhibits a variant FGFR2 protein. In some examples, the inhibitory effect of the compound is determined by direct assessment of tyrosine kinase activity. In additional examples, the inhibitory effect is determined by other assays, such as cell growth, apoptosis, or tumor metastasis assays, such as those described herein.

D. Detection of Altered Expression of FGFR2 Variants

Disclosed herein are methods of identifying subjects (such as a mammal, for example a human subject) for treatment with an inhibitor of FGFR2 to induce tumor cell death, inhibit tumor growth, or decrease risk of metastasis of a tumor cell, including determining altered expression of variant FGFR2 nucleic acid or protein in a sample from the subject (such as a blood or tissue sample, for example, a tumor biopsy). In particular examples, the variant includes a variant amino acid sequence at position(s) 536, 538, 548, 550, 565, 566, 618, 770 of SEQ ID NO: 2, or a combination of two or more thereof. In some examples, the subject has a variant FGFR2 that comprises a variant amino acid in the tyrosine kinase domain. In some examples, expression of the variant FGFR2 is compared to expression of FGFR2 in a normal control. In other examples, expression of the variant FGFR2 is compared to expression of FGFR2 in a cancer cell that does not express a variant FGFR2 molecule.

In particular examples, an increase in expression of a variant FGFR2 molecule relative to a control (such as FGFR2 expression in a cancer free tissue) indicates that the subject is a candidate for treatment with an inhibitor of that FGFR2 variant to induce tumor cell death, inhibit tumor growth, or decrease risk of metastasis of a tumor cell.

Such analysis can be based on PCR-based assays for these mutations, using for instance quantitative real-time PCR. See e.g. Bange et al., Cancer Res. 62:840-847, 2002. In some examples, primers and probes comprise at least 15 contiguous nucleotides of SEQ ID NO: 1.

In addition, overexpression of FGFR2 proteins may be detected through novel epitopes recognized by polyclonal and/or monoclonal antibodies used in ELISA, immunoblotting, flow cytometric, immunohistochemical and other mutant protein detection strategies (Wong et al., Cancer Res., 46: 6029-6033, 1986; Luwor et al., Cancer Res., 61: 5355-5361, 2001; Mishima et al., Cancer Res., 61: 5349-5354, 2001; Ijaz et al., J. Med. Virol., 63: 210-216, 2001)

In the present invention, a panel of FGFR2 kinase mutations were identified, more importantly these mutations are associated with drug resistance, such as, FGFR2 inhibitors. Such a panel of FGFR2 kinase mutation is useful as markers for cancer treatment in personalized medicine. The FGFR2 kinase mutations, as disclosed, comprise M536I, M538I, I548V, N550H, N550K, N550S, V565I, E566G, L618M, E719G, and Y770IfsX14.

III. FGFR2 Inhibitors

The methods disclosed herein include identifying a subject as a candidate for treatment with an inhibitor of FGFR2 to induce tumor cell death, reduce tumor growth, or decrease risk of tumor metastasis. Inhibitors of growth factor receptors may be any agent including a pharmaceutically active ingredient or pharmaceutically acceptable salt thereof, a drug, a toxin, a chemical, a small organic molecule, a large molecule or peptide or an antibody.

A. Small Molecule Inhibitors

Some small molecule inhibitors may inhibit multiple growth factor receptors, while others may be specific for a particular family of growth factor receptor (for example, FGFRs), and still others may be specific for one growth factor receptor subtype (such as FGFR1, FGFR2, FGFR3, or FGFR4). In particular examples, a small molecule inhibitor specifically inhibits FGFR2 activity (such as TK activity). In still further examples, the small molecule inhibitor specifically inhibits one or more FGFR2 variants.

In some examples, the small molecule inhibitor of FGFR2 variants is a previously identified growth factor receptor or FGFR inhibitor, including TKI258 (4-amino-5-fluoro-3-[5-

(4-methylpiperazin-1-yl)-1H-benzimidazol-2-yl]quin-olin-2 (1H)-one, also known as CHIR-258); PD173074 (1-tert-bu-tyl-3-[6-3,5-dimethoxyphenyl)-2-(4-diethylamino-butylamino)-pyrido[2,3-d]pyrimidin-7-yl]-urea; SU5402 (3-[3-(2-Carboxyethyl)-4-methylpyrrol-2-methylidenyl]-2-indolinone). Additional FGFR inhibitors may be identified utilizing the methods described herein. FGFR inhibitors include those that bind the active state of the receptor and those that bind the inactive state of the receptor.

In additional examples, inhibitors of FGFRs may include FGFR2-specific binding agents, such as polyclonal or monoclonal antibodies. Specific examples of FGFR2-specific binding agents are FGFR2-specific antibody or a functional fragment thereof, for instance monoclonal antibodies or fragments of monoclonal antibodies. Optionally, such monoclonal antibodies recognize an epitope of a variant FGFR2 (such as an epitope of a variant FGFR2 having an amino acid substitution in at least one position, including, but not limited to, amino acid(s) 536, 538, 548, 550, 550, 550, 565, 566, 618, 770 of SEQ ID NO: 2, or a combination thereof), and not (or to a lesser extent) an epitope of wild type FGFR2.

B. Large Molecules or Peptide Inhibitors

Large-molecule pharmaceuticals refer to pharmaceutical agents having a molecular weight greater than about 1000 daltons, e.g. peptidic drugs, vaccines and hormones. Many pharmaceutical agents are large molecules, for example, insulin, heparin, low molecular weight heparin (molecular weight less than about 5000 daltons), hirulog, hirugen, hirudin, interferons, cytokines, mono and polyclonal antibodies, immunoglobins, chemotherapeutic agents, vaccines, glycoproteins, bacterial toxins, hormones, calcitonins, glucagon like peptides (GLP-1), large molecular antibiotics (i.e., greater than about 1000 daltons), protein based thrombolytic compounds, platelet inhibitors, DNA, RNA, gene therapeutics, antisense oligonucleotides, opioids, narcotics, hypnotics, steroids and pain killers. When used herein, "dalton" means 1/12 the mass of the nucleus of carbon-12 (i.e. equivalent to 1.657.times.10.sup.-24 grams, also known as an "atomic mass unit"). Peptides are short polymers formed from the linking of amino acids and comprise, some of the basic components of human biological processes, including enzymes, hormones, and antibodies. The link between one amino acid residue and the next is known as a peptide bond or an amide bond, Proteins, by contrast, are typically much longer chains of amino acids, similarly linked by peptide bonds. Preferred pharmaceutical agents that may be inhibitors to FGFR2 and its variants include large molecule drugs of varying sizes.

C. Antibody Inhibitors

The term "antibody" is used herein in the broadest sense and refers generally to a molecule that contains at least one antigen binding site that immunospecifically binds to a particular antigen target of interest. Antibody thus includes but is not limited to native antibodies and variants thereof, fragments of native antibodies and variants thereof, peptibodies and variants thereof, and antibody mimetics that mimic the structure and/or function of an antibody or a specified fragment or portion thereof, including single chain antibodies and fragments thereof. The term thus includes full length antibodies and/or their variants as well as immunologically active fragments thereof, thus encompassing, antibody fragments capable of binding to a biological molecule (such as an antigen or receptor) or portions thereof, including but not limited to Fab, Fab', F(ab')2, facb, pFc', Fd, Fv or scFv (See, e.g., CURRENT PROTOCOLS IN IMMUNOLOGY, (Colligan et al., eds., John Wiley & Sons, Inc., NY, 1994-2001).

Monoclonal or polyclonal antibodies may be produced to either the normal FGFR2 protein or mutant forms of this protein, for instance particular portions that contain a mutation and therefore may provide a distinguishing epitope. Optimally, antibodies raised against these proteins or peptides would specifically detect the protein or peptide with which the antibodies are generated. That is, an antibody generated to the FGFR2 protein or a fragment thereof would recognize and bind the FGFR2 protein and would not substantially recognize or bind to other proteins found in human cells. In some embodiments, an antibody is specific for (or measurably preferentially binds to) an epitope in a variant protein versus the wild type protein, or vice versa, as discussed more fully herein.

D. Pharmaceutical Composition Comprising FGFR Inhibitor

Disclosed herein are methods of slowing the growth of cancer cells using pharmaceutical compositions comprising an FGFR inhibitor and/or derivatives thereof as an ingredient in a pharmaceutical composition to be used in combination with a test to determine whether the FGFR expressed by a tumor is susceptible to the composition. Such pharmaceutical compositions may take any physical form necessary depending on a number of factors including the desired method of administration and the physicochemical and stereochemical form taken by the compound or pharmaceutically acceptable salts of the compound. Such physical forms include a solid, liquid, gas, sol, gel, aerosol, or any other physical form now known or yet to be disclosed. The concept of a pharmaceutical composition containing the compound also encompasses an FGFR inhibitor, or a pharmaceutically acceptable salt thereof, or without any other additive. The physical form of the pharmaceutical composition may affect the route of administration and one skilled in the art would know to choose a route of administration that takes into consideration both the physical form of the compound and the disorder to be treated. Pharmaceutical compositions may be prepared using methodology well known in the pharmaceutical art. A pharmaceutical composition may include a second effective compound of a distinct chemical formula from the compound. This second effective compound may have the same or a similar molecular target as the target of the compound, or it may act upstream or downstream of the molecular target of the compound with regard to one or more biochemical pathways.

Pharmaceutical compositions include materials capable of modifying the physical form of a dosage unit. In one nonlimiting example, the composition includes a material that forms a coating that surrounds and/or contains the compound. Materials that may be used in such a coating, include, for example, sugar, shellac, gelatin, or any other inert coating agent.

Pharmaceutical compositions may be prepared as a gas or aerosol. Aerosols encompass a variety of systems including colloids and pressurized packages. Delivery of a composition in this form may include propulsion of a pharmaceutical composition containing the compound through use of liquefied gas or other compressed gas or by a suitable pump system. Aerosols may be delivered in single phase, bi-phasic, or tri-phasic systems.

In some aspects of the invention, the pharmaceutical composition is in the form of a solvate. Such solvates are produced by the dissolution of the compound in a pharmaceutically acceptable solvent. Pharmaceutically acceptable solvents include any mixtures of more than one solvent. Such solvents may include pyridine, chloroform, propan-1-ol, ethyl oleate, ethyl lactate, ethylene oxide, water, ethanol, and any other solvent that delivers a sufficient quantity of the compound to treat the affliction without serious complications arising from the use of the solvent in a majority of patients.

Pharmaceutical compositions may also include a pharmaceutically acceptable carrier. Carriers include any substance that may be administered with the compound with the intended purpose of facilitating, assisting, or helping the administration or other delivery of the compound. Carriers include any liquid, solid, semisolid, gel, aerosol or anything else that may be combined with the compound to aid in its administration. Examples include diluents, adjuvants, excipients, water, and oils (including petroleum, animal, vegetable or synthetic oils). Such carriers include particulates such as a tablet or powder, liquids such as an oral syrup or injectable liquid, and inhalable aerosols. Further examples include saline, gum acacia, gelatin, starch paste, talc, keratin, colloidal silica, and urea. Such carriers may further include binders such as ethyl cellulose, carboxymethylcellulose, microcrystalline cellulose, or gelatin; excipients such as starch, lactose or dextrins; disintegrating agents such as alginic acid, sodium alginate, Primogel, and corn starch; lubricants such as magnesium stearate or Sterotex; glidants such as colloidal silicon dioxide; sweetening agents such as sucrose or saccharin, a flavoring agent such as peppermint, methyl salicylate or orange flavoring, or coloring agents. Further examples of carriers include polyethylene glycol, cyclodextrin, oils, or any other similar liquid carrier that may be formulated into a capsule. Still further examples of carriers include sterile diluents such as water, saline solution, physiological saline, Ringer's solution, isotonic sodium chloride, fixed oils such as synthetic mono or diglycerides, polyethylene glycols, glycerin, cyclodextrin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose, thickening agents, lubricating agents, and coloring agents.

The pharmaceutical composition may take any of a number of formulations depending on the physicochemical form of the composition and the type of administration. Such forms include solutions, suspensions, emulsions, tablets, pills, pellets, capsules, capsules containing liquids, powders, sustained-release formulations, directed release formulations, lyophylates, suppositories, emulsions, aerosols, sprays, granules, powders, syrups, elixirs, or any other formulation now known or yet to be disclosed. Additional examples of suitable pharmaceutical carriers are described in "Remington's Pharmaceutical Sciences" by E. W. Martin, hereby incorporated by reference in its entirety.

Methods of administration include, but are not limited to, oral administration and parenteral administration. Parenteral administration includes, but is not limited to intradermal, intramuscular, intraperitoneal, intravenous, subcutaneous, intranasal, epidural, sublingual, intranasal, intracerebral, intraventricular, intrathecal, intravaginal, transdermal, rectally, by inhalation, or topically to the ears, nose, eyes, or skin. Other methods of administration include but are not limited to infusion techniques including infusion or bolus injection, by absorption through epithelial or mucocutaneous linings such as oral mucosa, rectal and intestinal mucosa. Compositions for parenteral administration may be enclosed in ampoule, a disposable syringe or a multiple-dose vial made of glass, plastic or other material.

Administration may be systemic or local. Local administration is administration of the compound to the area in need of treatment. Examples of local infusion during surgery; topical application, by local injection; by a catheter; by a suppository; or by an implant. Administration may be by direct injection at the site (or former site) of a cancer, tumor, or precancerous tissue or into the central nervous system by any suitable route, including intraventricular and intrathecal injection. Intraventricular injection can be facilitated by an intraventricular catheter, for example, attached to a reservoir, such as an Ommaya reservoir. Pulmonary administration may be achieved by any of a number of methods known in the art. Examples include use of an inhaler or nebulizer, formulation with an aerosolizing agent, or via perfusion in a fluorocarbon or synthetic pulmonary surfactant. The compound may be delivered in the context of a vesicle such as a liposome or any other natural or synthetic vesicle. Alternatively, the compound may be delivered by intrauterine devices similar to the Mirena® intrauterine system (Bayer Pharmaceuticals)

A pharmaceutical composition intended to be administered by injection may be prepared by dissolving the compound with water so as to form a solution. In addition, a surfactant may be added to facilitate the formation of a homogeneous solution or suspension. Surfactants include any complex capable of non-covalent interaction with the compound so as to facilitate dissolution or homogeneous suspension of the compound.

Pharmaceutical compositions may be prepared in a form that facilitates topical or transdermal administration. Such preparations may be in the form of a solution, emulsion, ointment, gel base, transdermal patch or iontophoresis device. Examples of bases used in such compositions include petrolatum, lanolin, polyethylene glycols, beeswax, mineral oil, diluents such as water and alcohol, and emulsifiers and stabilizers, thickening agents, or any other suitable base now known or yet to be disclosed.

Appropriate dosages for treatment with small organic molecules or antibodies can be determined by one of skill in the art. In general, an effective amount of a composition that includes a FGFR2 small molecule or antibody inhibitor administered to a subject will vary depending upon a number of factors associated with that subject, for example the overall health of the subject, the condition to be treated, or the severity of the condition. An effective amount of a composition that includes a FGFR2 inhibitor can be determined by varying the dosage of the compound and measuring the resulting therapeutic response, such as the decrease in metastasis of cancer, or the decrease in the size, volume or number of tumors. FGFR2 inhibitors can be administered in a single dose, or in several doses, as needed to obtain the desired response. However, the effective amount can be dependent on the source applied, the subject being treated, the severity and type of the condition being treated, and the manner of administration. In some examples, the dose of a FGFR2 inhibitor administered to a subject may be about 0.1 mg/kg to about 1000 mg/kg. In particular examples, the dose may be about 1 mg/kg to about 100 mg/kg, such as about 40 mg/kg.

In a further example, a therapeutically effective dose of a FGFR2 inhibitor includes daily use for at least about three months, such as at least about three months, about six months, about one year, about two years, about three years, about four years, or about five years.

Pharmaceutical compositions comprising an FGFR2 inhibitor can be administered alone, in the presence of a pharmaceutically acceptable carrier, in the presence of other therapeutic agents (for example other anti-cancer therapeutic agents), or both. Such anti-cancer therapeutics include, but are not limited to, chemotherapeutic drug treatment, radiation, gene therapy, hormonal manipulation, immunotherapy and antisense oligonucleotide therapy. Examples of useful chemotherapeutic drugs include, but are not limited to, hydroxyurea, busulphan, cisplatin, carboplatin, chlorambucil, melphalan, cyclophosphamide, Ifosphamide, danorubicin, doxorubicin, epirubicin, mitoxantrone, vincristine, vinblastine, Navelbine® (vinorelbine), etoposide, teniposide, paclitaxel, docetaxel, gemcitabine, cytosine, arabinoside, bleomycin, neocarcinostatin, suramin, taxol, mitomycin C, and the like. The compounds of the invention are also suitable for use with standard combination therapies employing two or more chemotherapeutic agents. It is to be understood that anti-cancer therapeutics for use in the present invention also include novel compounds or treatments developed in the future.

Further, addition of a pharmaceutical composition to cancer cells includes all actions by which a pharmaceutical composition is placed into sufficiently close proximity to a cancer cell that the effect of the pharmaceutical composition on the cancer cell is realized. The type of addition chosen will depend upon whether the cancer cells are in vivo, ex vivo, or in vitro, the physical or chemical properties of the pharmaceutical composition, and the effect the composition is to have on the cancer cell. Nonlimiting examples of addition include addition of a solution containing the pharmaceutical composition to tissue culture media in which in vitro cancer cells are growing; any method by which a pharmaceutical composition may be administered to an animal including intravenous, parenteral, or any other of the methods of administration; or the activation or inhibition of cells that in turn have effects on the cancer cells, such as immune cells like macophages and CD8+ T cells, or endothelial cells that may differentiate into blood vessel structures in the process of angiogenesis or vasculogenesis.

Cancer cells may display abnormal cell growth characterized as hyperplasia, metaplasia, or dysplasia, the presence of one or more characteristics of a transformed phenotype, or of a malignant phenotype, displayed in vivo or displayed in vitro by a cell sample derived from a patient can indicate the desirability of prophylactic/therapeutic administration of the composition of the invention. Such characteristics of a transformed phenotype include but not limited to morphology changes, looser substratum attachment, loss of contact inhibition, loss of anchorage dependence, protease release, increased sugar transport, decreased serum requirement, expression of fetal antigens. Further examples include leukoplakia (in which a benign-appearing hyperplastic or dysplastic lesion of the epithelium presents), or Bowen's disease (a carcinoma in situ), and are pre-neoplastic lesions indicative of the desirability of prophylactic intervention. In another example, fibrocystic disease (including cystic hyperplasia, mammary dysplasia, adenosis, or benign epithelial hyperplasia) is indicative of the desirability of prophylactic intervention.

Determination of an effective amount of the compound is within the capability of those skilled in the art, especially in light of the detailed disclosure provided herein. The effective amount of a pharmaceutical composition used to effect a particular purpose, as well as its toxicity, excretion, and overall tolerance may be determined in cell cultures or experimental animals by pharmaceutical and toxicological procedures either known now by those skilled in the art or by any similar method yet to be disclosed. One example is the determination of the $IC_{50}$ (half maximal inhibitory concentration) of the pharmaceutical composition in vitro in cell lines or target molecules. Another example is the determination of the $LD_{50}$ (lethal dose causing death in 50% of the tested animals) of the pharmaceutical composition in experimental animals. The exact techniques used in determining an effective amount will depend on factors such as the type, physical and/or chemical properties of the pharmaceutical composition, the property being tested, and whether the test is to be performed in vitro or in vivo. The determination of an effective amount of a pharmaceutical composition will be well known to one of skill in the art who will use data obtained from any tests in making that determination. Determination of an effective amount of compound for addition to a cancer cell also includes the determination of an effective therapeutic amount, including the formulation of an effective dose range for use in vivo, including in humans.

The effective amount of the pharmaceutical composition that results in the slowing of expansion of the cancer cells would preferably result in a concentration at or near the target tissue that is effective in slowing cellular expansion in neoplastic cells, but have minimal effects on non-neoplastic cells, including non-neoplastic cells exposed to radiation or recognized chemotherapeutic chemical agents. Concentrations that produce these effects can be determined using, for example, apoptosis markers such as the apoptotic index and/or caspase activities either in vitro or in vivo.

Pharmaceutical compositions may be administered prior to, concurrently with, or after administration of a second pharmaceutical composition. If the compositions are administered concurrently, they are administered within one minute of each other. If not administered concurrently, the second pharmaceutical composition may be administered a period of one or more minutes, hours, days, weeks, or months before or after the pharmaceutical composition that includes the compound.

Alternatively, a combination of pharmaceutical compositions may be cyclically administered. Cycling involves the administration of one or more pharmaceutical compositions for a period of time, followed by the administration of one or more different pharmaceutical compositions for a period of time and repeating this sequential administration, in order to reduce the development of resistance to one or more of the compositions, to avoid or reduce the side effects of one or more of the compositions, and/or to improve the efficacy of the treatment.

In the present invention, a panel of FGFR2 kinase mutations were identified as associated with drug resistance, such as, FGFR2 inhibitors including, but not limited to, dovitinib, PD173074, AZD4547, ponatinib, BGJ398, and DCC2036. Such a panel of FGFR2 kinase mutation is useful as markers for cancer treatment in personalized medicine. The FGFR2 kinase mutations, as disclosed, comprise M536I, M538I, I548V, N550H, N550K, N550S, V565I, E566G, L618M, E719G, and Y770IfsX14. Among these markers, the presence of N550K FGFR2 kinase mutation variant is associated with drug resistance to dovitinib and AZD4547; whereas the presence of N550K FGFR2 kinase mutation variant is associated with the drug sensitivity to ponatinib and/or BGJ398; and the presence of V565I FGFR2 kinase mutation variant is associated with the drug sensitivity to AZD4547 and/or DCC2036 in the subject. Therefore, this panel of FGFR2 kinase mutation enables drug response identification and effective treatment application.

IV. Kits

The invention further encompasses kits that facilitate the administration of the pharmaceutical compositions. An example of such a kit includes one or more units of effective amounts or dosages of the compositions. The unit dosage would be enclosed in a preferably sterile container and would be comprised of the compound and a pharmaceutically acceptable carrier. In another aspect, the unit dosage would comprise one or more lyophilates of the compound. In this aspect of the invention, the kit may include another preferably sterile container enclosing a solution capable of dissolving the lyophilate. However, such a solution need not be included in the kit and may be obtained separately from the lyophilate. In another aspect, the kit may include one or more devices used in administrating the unit dosages or a pharmaceutical composition to be used in combination with the compound. Examples of such devices include, but are not limited to, a syringe, a drip bag, a patch or an enema. In some aspects of the invention, the kit comprises the container that encloses the unit dosage.

The kit may further comprise one or more reagents used to identify a candidate for treatment with a pharmaceutical composition comprising one or more inhibitors to FGFR2 mutation variants. The reagents in the kit may be primers, probes, and/or antibodies that are capable of identifying a FGFR2 mutation variant.

The kit that facilitates nucleic acid based assays may further comprise one or more of the following: nucleic acid extraction reagents, controls, disposable cartridges, labeling reagents, enzymes including PCR amplification reagents such as the DNA polymerases Taq or Pfu, reverse transcriptase, or one or more other polymerases, and/or reagents that facilitate hybridization.

In another embodiment, the kit may further comprise a label that can be used to label the primer or probe oligonucleotide. A label may be any substance capable of aiding a machine, detector, sensor, device, or enhanced or unenhanced human eye from differentiating a sample that that displays positive expression from a sample that displays reduced expression. Examples of labels include but are not limited to: a radioactive isotope or chelate thereof, a dye (fluorescent or nonfluorescent) stain, enzyme, or nonradioactive metal. Specific examples include but are not limited to: fluorescein, biotin, digoxigenin, alkaline phosphatase, biotin, streptavidin, $^3$H, $^{14}$C, $^{32}$P, $^{35}$S, or any other compound capable of emitting radiation, rhodamine, 4-(4'-dimethylaminophenylazo)benzoic acid ("Dabcyl"); 4-(4'-dimethylamino-phenylazo)sulfonic acid (sulfonyl chloride) ("Dabsyl"); 5-((2-aminoethyl)-amino)-naphtalene-1-sulfonic acid ("EDANS"); Psoralene derivatives, haptens, cyanines, acridines, fluorescent rhodol derivatives, cholesterol derivatives; ethylene diamine tetra-acetic acid ("EDTA") and derivatives thereof or any other compound that signals the presence of the labeled nucleic acid. In one embodiment of the invention, the label includes one or more dyes optimized for use in genotyping. Examples of such dyes include but are not limited to: dR110, 5-FAM, 6FAM, dR6G, JOE, HEX, VIC, TET, dTAMRA, TAMRA, NED, dROX, PET, BHQ+, Gold540, and LIZ.

In yet anther embodiment, the primers and probes in the kit may have been labeled, and can be applied without labeling process in PCR, sequencing reaction, or binding to a solid substrate such as oligonucleotide array.

The kit that facilitates the administration of the pharmaceutical compositions may also comprise instructions for use. In one embodiment, the kit may further comprise an indication that links the output of the assays provided by the kit to a particular result. For example, an indication may provide guide to associate the presence or absence of one or more sequences to a specific pharmaceutical composition. The output of the assay may be in a form of a particular sequence, a particular genotype, a particular ΔCt level in a real-time quantitative PCR reaction, a level of fluorescence or radioactive decay, a value derived from a standard curve, or from a positive or negative control, or any combination of these and other outputs. The indication may be printed on a writing that may be included in the kit or it may be posted on the Internet or embedded in a software package. The writing may include graphical depictions of results such as a photomicrograph or amplification plot.

The kit that facilitates the administration of the pharmaceutical compositions may further comprise a device used to collect the sample. Such devices may include but need not be limited to: swabs, needles, blood collection tubes, wipes, or any other apparatus that may be used to collect a biological sample from a subject.

EXAMPLE

The following non-limiting examples are included to illustrate the invention.

Example 1

Materials and Methods

Cell Lines and Reagents:

The BaF3 cells used in this study were obtained directly from ATCC and were passaged for fewer than 6 months after their receipt and as such reauthentification was not performed. The JHUEM-2, MFE280 and MFE296 cell lines was purchased from the RIKEN Cell Bank (Tsukuba, Japan), the DSMZ (Berlin, Germany) and the European Collection of Cell Cultures (Salisbury) respectively. AN3CA, HEC1A, Ishikawa, and KLE were provided by Dr. Paul Goodfellow (Washington University, St. Louis, Mo.). EI, EJ and EN1078D were provided by Dr Gordon Mills (MD Anderson Cancer Center, Houston, Tex.). Recombinant murine IL3 and human FGF10 were purchased from R&D Systems (Minneapolis, Minn.). Dovitinib and ponatinib were purchased from Selleck Chemicals (Houston, Tex.) and PD173074 was purchased from EMD Chemicals (Gibbstown, N.J.). Phospho-FGFR (P-FGFR) antibody was purchased from Cell Signaling Technology (Genesearch Pty Ltd, Arundel, Australia), total FGFR2 (TFGFR) antibody was purchased from Santa Cruz Biotechnology (Thermo FisherScientific Pty Ltd, Scoresby, Australia), α-tubulin antibody was purchased from Sigma-Aldrich (Castle Hill, NSW, Australia) and IRDye 800 and IRDye 680LT secondary antibodies were purchased from Rockland (Jomar Biosciences Pty Ltd, Kensington, Australia).

BaF3 Screen for Dovitinib-Resistant FGFR2 Mutations:

BaF3 cells were stably transduced with pEF1a.FGFR2b.IRES.neo, pEF1a.FGFR2b.S252W.IRES.neo, or pEF1a.FGFR2b.N550K.IRES.neo plasmid DNA using Amaxa nucleofection and selected for 14 days in 1200 µg/ml G418, as previously reported. Stably selected cells were plated at a density of 1×105 and 4×105 cells/well in six 96 well plates each in BaF3 growth media without IL3, supplemented with 1 nM FGF10 and 5 µg/ml heparan sulphate. Dovitinib was added to duplicate plates of each cell density at 5, 10, or 15× the IC50 (100, 200, 300 nM, respectively for FGFR2b and S252W expressing cells, and 2000, 4000, 6000 nM, respectively, for N550K expressing cells). Fresh FGF10 and heparan sulphate were added every 2-3 days. Colonies that grew out were expanded in media with FGF10 and heparan sulphate and genomic DNA extracted using the GenElute Mammalian Genomic DNA Miniprep kit (Sigma-Aldrich, St. Louis, Mo.). Inserted human FGFR2b was amplified using overlapping primer pairs and sequenced in two directions for mutations in the intracellular domain of FGFR2b (sequencing primers available upon request). Mutations were confirmed in an independent PCR. Amino acid substitutions are listed according to isoform 2 of human FGFR2 (FGFR2b) (NP_075259.4).

Site-Directed Mutagenesis:

Each putative dovitinib-resistant mutation was introduced into full-length FGFR2b by site-directed mutagenesis (SDM). Briefly, SDM was performed on 50 ng of pEF1a.FGFR2b.IRES.neo plasmid DNA using the QuikChange II XL Site-Directed Mutagenesis kit (Agilent Technologies, Santa Clara, Calif.). Plasmid DNA was isolated using the Plasmid DNA Miniprep Kit (Qiagen, Valencia, Calif.) and diagnostic restriction digests performed. Plasmid DNA was then isolated from SDM-positive clones using the Qiagen EndoFree Plasmid MaxiPrep kit (Qiagen, Valencia, Calif.). Mutations were confirmed by sequencing of the entire coding region of FGFR2b.

Generation of BaF3 cells Stably Expressing Dovitinib-Resistant FGFR2b Mutations:

pEF1a.FGFR2b.IRES.neo or the various FGFR2b mutant plasmids were introduced into BaF3 cells using the Amaxa nucleofector kit V, according to the manufacturer's instructions (Amaxa, Walkersville, Md.). Cells were selected in growth media containing 1200 µg/ml G418 and 5 ng/ml IL3 for 14 days and frozen down. Proliferation assays in the presence or absence of drug were performed in BaF3 cells that had not been passaged for more than 5 weeks after this initial freeze.

Generation of JHUEM-2 cells Stably Expressing Wild-type and Mutant FGFR2b:

JHUEM-2 cells were infected with lentiviral particles containing pEF1α.FGFR2b.IRES.neo plasmids encoding wild-type FGFR2b, FGFR2bY376C or FGFR2bN550K. A JHUEM-2 line was also infected with an empty pEF1α.IRES.neo vector as a control. Cells were then selected in growth media containing 900 µg/mL G418 for 14 days and frozen down.

IC50 Analysis:

BaF3 cells expressing wild-type or mutant FGFR2b were plated at either 3000 or 10,000 cells per well in 96 well plates in BaF3 media without IL3, supplemented with 1 nM FGF10 and 5 µg/ml heparan sulphate. Dovitinib and PD173074 were added at half-log dilutions ranging from 10 µM-3 nM, while ponatinib was added at half-log dilutions ranging from 1 µM-0.1 nM respectively. After 72 hours, cell viability was measured using the ViaLight kit (Lonza, Walkersville, Md.). Values were normalized to DMSO vehicle control wells and IC50 values generated by nonlinear regression analysis with variable slope using Prism software version 4.0c (GraphPad Software, San Diego, Calif.). For the ponatinib experiments, 3000 cells per well were seeded and assayed in triplicate on two independent days. As biological replicate data for dovitinib and PD173074 had been generated with 10000 cells per well, these assays were repeated a third time with 3000 cells per well with no significant differences observed and the presented IC50 values are the replicates of these three independent experiments. Parental endometrial cancer cell lines and stably transfected JHUEM-2 cells were seeded at 3,000 cells per well in 96 well plates in their individual growth media. After 24 hours, dovitinib, PD173074 and ponatinib were added at half-log dilutions (1 nM to 10 µM). Following 72 hours of drug treatment, cell viability was assessed using the CyQUANT Cell Proliferation Assay Kit (Life Technologies, Carlsbad, Calif.). Values were normalized to DMSO vehicle control wells and IC50 values calculated as described above. Proliferation assays were performed in triplicate on two independent days and the results averaged.

Receptor Phosphorylation in Response to Ligand Treatment:

BaF3 cells expressing wild-type or mutant FGFR2 were washed twice in media minus IL3. Cells were then resuspended in 200 µL of BaF3 media minus IL3 containing 5 µg/mL heparan sulphate and 16 nM FGF10 for 7.5 minutes. Cells were centrifuged at 1000 rpm for 5 minutes, the supernatant discarded and the cell pellet resuspended in 200 µL lysis buffer (1% Triton X-100, 50 mM Tris-HCl (pH 7.4), 150 mM NaCl, 2 mM Na3VO4 and 10 mM NaF). The protein concentration was determined using a BioRad quick start kit. A total of 150 µg of protein was subjected to SDS-gel electrophoresis on a 4-12% bis-acrylamide gradient gel, transferred to a nitrocellulose membrane, blocked with odyssey blocking buffer and incubated with the primary antibody diluted in Odyssey blocking buffer overnight at 4° C. The membranes were washed with TBS-T and incubated with the secondary antibody diluted in Odyssey blocking buffer for 1 hour at room temperature. After another washing step the membrane was scanned using a Lycor flat bed scanner.

Inhibition of Receptor Phosphorylation in Response to Ligand:

BaF3 cells expressing wild-type or mutant FGFR2 were grown in T75 flasks in 50 mL BaF3 media. Cells were washed twice with IL3-free media, resuspended in 35 mL IL3-free media, and the cells evenly split into seven T25 flasks. An FGFR inhibitor was added to final concentrations of 1, 10, 30, 100, 300, 1000 nM or DMSO control corresponding to the highest FGFR inhibitor concentration (0.01% v/v). Cells were incubated with the inhibitors for 90 minutes at 37° C., pelleted at 1000 rpm, and the pellet was resuspended in BaF3 media minus IL3 containing 5 µg/mL heparan sulphate and 16 nM FGF10 for 7.5 minutes. After the incubation period, cells were centrifuged at 1000 rpm for 5 minutes, the supernatant discarded and the cells resuspended in 200 µL lysis buffer. The cell lysates were processed and subjected to SDS gel electrophoresis as described above.

Protein Expression and Purification:

The cDNA fragment encoding residues P459 to E769 of human FGFR2c (Accession code: NP_075259) was amplified by PCR and subcloned into pET bacterial expression vector with an NH2-terminal 6×His-tag to aid in protein purification. Point mutations (M536I, M538I, I548V, N550H, N550K, N550S, V565I, E566G, L618M and K660E) were introduced using QuikChange site-directed mutagenesis kit (Stratagene). The bacterial strain BL21 (DE3) cells were transformed with the expression constructs, and kinase expression was induced with 1 mM isopropyl-L-thio-B-D-galactopyranoside overnight at the appropriate temperature. The cells were lysed, and the soluble kinase proteins were purified accordingly. N-terminally His-tagged substrate peptide consisting of residues L762 to T822 of FGFR2 was expressed and purified similar to the kinase domain. The substrate peptide corresponds to the C-terminal tail of FGFR2 and contains five authentic tyrosine phosphorylation sites (Y770, Y780, Y784, Y806, Y813).

Kinase Assay:

Wild-type and mutated FGFR2 kinases were mixed with reaction solutions containing ATP, MgCl2 and the substrate peptide. The final concentrations of the reaction mix are: kinase 0.5 mg/mL, substrate 2.17 mg/ml, ATP 10 mM and MgCl2 20 mM. The reactions were quenched at different time points by adding 100 mM EDTA. The progress of the substrate phosphorylation was followed by native-PAGE, and tyrosine phosphorylation content of the substrate peptide was quantified by timeresolved MALDI-TOF mass spectrometry using a Bruker Autoflex mass spectrometer operated in linear mode according to the published protocol by comparing signals from phosphorylated and the cognate non-phosphorylated peptides.

In Vitro Kinase Inhibition Assay:

Wild-type FGFR2 kinase and the N550H and V565I mutants were incubated for 5 minutes with reaction solutions containing ATP, MgCl2 and increasing concentrations of either dovitinib or ponatinib. The final concentrations of kinase, ATP and MgCl2 were 90 µM, 5.33 mM, 10.66 mM, respectively. The molar ratios of kinase:inhibitor in the reaction mix were 1:0, 1:0.2, 1:0.5, 1:1, 1:2, 1:5 or 1:10. The reactions were quenched by adding EDTA to a final concentration of 69.6 mM, and the progress of the kinase autophosphorylation/inhibition was monitored by native-PAGE.

Example 2

Mutations Identified in TKI258-Resistant BaF3.FGFR2b Clones

The BaF3 cell line is an IL-3 dependent murine pro-B cell line that is commonly employed to model TKI resistant mutations. BaF3 cells are made dependent on a specific oncogenic tyrosine kinase, and are cultured in the presence of a kinase inhibitor against that specific kinase, and resistant colonies can be screened for drug resistant mutations. This approach has been successfully used to identify tyrosine kinase inhibitor (TKI)-resistant mutations in Bcr-Abl, FLT3, PDGFRA, MET, EGFR and JAK2 and has effectively reproduced the pattern and relative abundance of Bcr-Abl mutations seen clinically in imatinib-resistant patients.

BaF3 cells stably expressing the 'b' splice isoform of FGFR2 (FGFR2b, NM_022970) were used. The selected BaF3-FGFR2b cells were stably plated in 96 well plates at 1×10$^5$ and 4×10$^5$ cells/well. The growth media contains (−) IL3, 1 nM FGF10, 5 µg/ml heparin. TKI258 (dovitinib, Selleck Chemicals) was added at IC$_{50}$×5, ×10, ×15. Fresh 1 nM FGF10 with 5 µg/ml heparin were added 3 times per week. Colonies that grew out in the presence of TK1258 were selected and those selected colonies were expanded in the presence of 1 nM FGF10 and 5 µg/ml heparin. Of the 3×10$^8$ cells plated, 63 resistant clones were isolated.

Genomic DNA was isolated from the BaF3.FGFR2b colonies selected in the TKI258-resistance screen. Exons encoding the intracellular domain of FGFR2b were amplified and sequencing performed in two directions. Mutations in the intracellular domain of FGFR2b were identified in 26 of the 63 (41%) TKI258 resistant BaF3.FGFR2b clones. Among the 26 FGFR2b mutations, eleven different mutation variants were detected (Table 1). The eleven different mutation variants are: M536I, M538I, I548V, N550H, N550K, N550S, V565I, E566G, L618M, E719G, and Y770IfsX14. The most commonly mutated codon was N550, with mutations occurring in 19 of the 26 (73%) resistant clones. In addition, E719G mutation variant was identified in a clone with a N550H mutation; E719G mutation alone did not induce resistance to TKI258 or PD173074. There was an increase in mutation frequency with selective pressure, with an average of 20% mutation frequency in resistant clones selected at 5×IC$_{50}$ and an average of 67% mutation frequency in resistant clones selected at 15×10$_{50}$.

TABLE 1

| TKI258 resistant FGFR2b variants: | |
|---|---|
| Mutation Identified | Mutation Incidence |
| M536I | 1 |
| M538I | 1 |
| I548V | 1 |
| N550H | 17 |
| N550K | 1 |
| N550S | 1 |
| V565I** | 1 |
| E566G | 1 |
| L618M | 1 |
| E719G | 1 |
| Y770IfsX14 | 1 |

**Gatekeeper mutation

Example 3

BaF3/FGFR2b Mutants' Enhanced TKI Resistance and Receptor Activation Compared to Wildtype BaF3/FGFR2b wildtype and N550K mutation variant cells were plated at a density of 10,000 cells/well in a 96-well plate. TKI258 (Selleck Chemicals) or PD173074 (Calbiochem) was added in half-log dilutions in the absence of IL3 and in the presence of 1 nM FGF10 and 5 µg/mL heparin. After 72 hours, cell viability was measured using the ViaLight assay from Lonza (Visp, CH). The IC$_{50}$ values shown in FIG. 1 were normalized to DMSO control and data were analyzed with Prism software. The IC$_{50}$ value of TKI258 in BaF3/FGFR2b wildtype is 23.9 in comparison to 418.9 in N550K resistance cells, a nearly 20-fold difference. The IC$_{50}$ value of PD173074 in BaF3/FGFR2b wildtype is 4.5 in comparison to 775.6 in N550K resistance cells, over 170-fold difference.

Figure 2:
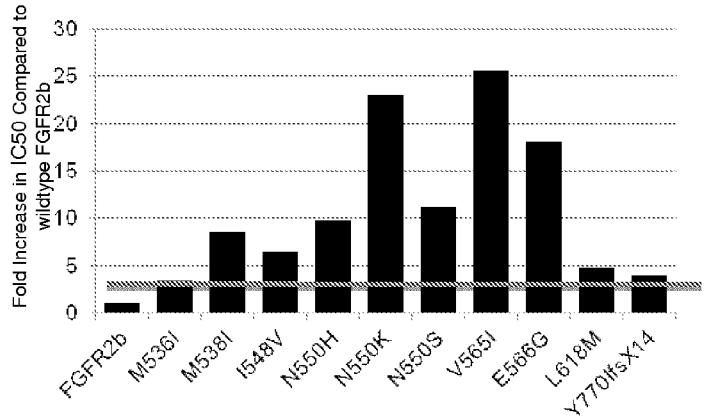
FIG. 2 depicts that the mutations result in resistance to TKI258 and PD173074 and that the mutations result in enhanced receptor activation in the presence of FGF ligand.
Figure 2:
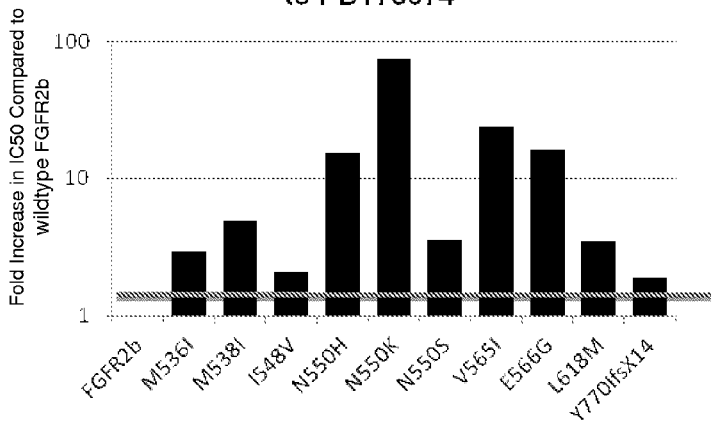
Figure 2:
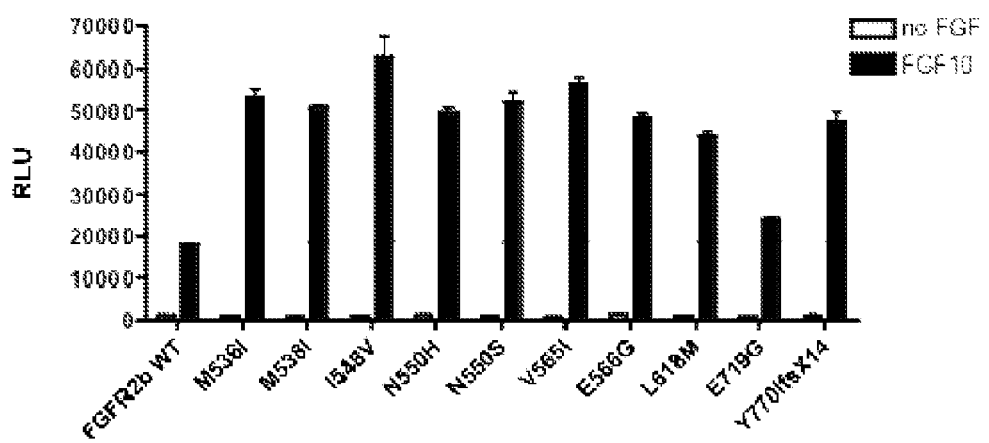

Similar tests were performed with the other 10 FGFR2b mutation variants. The majority of the mutations identified in this drug resistance screen result in activation of FGFR2. FIG. 2A showed the FGFR2 mutations confer resistance to TKI258 (dovitinib). The fold increase in IC$_{50}$ compared to wildtype FGFR2 ranges from about 3-4 fold to about 25 fold, with V565I being the most resistant and M536I being the least resistant. The FGFR2 mutations resistance to another TKI PD173074 was also tested. In contrast to TKI285, the fold increase in IC$_{50}$ to PD173074 compared to wildtype FGFR2 is in a much wider range, as shown in FIG. 2B, with N550K being the most resistant and Y770IfsX14 being the least resistant to PD173074. The receptor activation of FGFR2 mutants and wildtype were measured and compared in the presence of FGF ligand. FIG. 2C shows the enhanced receptor activation of all FGFR2 mutant variants.

Example 4

Parallel Dovitinib Resistance Screens Using BaF3 Cells Carrying FGFR2 Activating Mutations Parallel dovitinib resistance screens using BaF3 cells expressing either of the FGFR2 activating mutations, S252W or N550K were also performed. The S252W mutation is the most common FGFR2 mutation seen in endometrial tumors and maps to the extracellular ligand-binding region of FGFR2. Structural and biochemical studies have shown that this mutation results in ligand-dependent receptor activation by introducing additional contacts between FGFR and FGF ligand, and therefore, it was not expected that there is a different pattern of resistance mutations. N550K is the second most common FGFR2 mutation identified in endometrioid endometrial cancer. It was shown in the study herein that this mutation activates the kinase. BaF3 cells expressing S252W mutant FGFR2 show similar dovitinib sensitivity to BaF3 cells expressing wild-type FGFR2 and were thus treated in a similar manner with 100, 200, or 300 nM dovitinib. Resistant clones grew out in 51/384 wells and the FGFR2 kinase domain was sequenced in thirty-five resistant clones that grew out at the two highest dovitinib concentrations. FGFR2 mutations were identified in four clones affecting three amino acids: N550T, E566A (two independent clones), and K642N. Although a reduced mutation rate in the resistant BaF3.FGFR2 S252W BaF3 clones was observed, the presence of the S252W mutation did not dramatically alter the spectrum of dovitinib-resistant mutations identified as two of these codons (N550, E566) were also mutated in the wild-type FGFR2 BaF3 screen. Moreover, all three mutations were confirmed to confer resistance to dovitinib when expressed in conjunction with the activating S252W mutation in proliferation assays. For the N550K resistance screen, BaF3 cells expressing N550K mutant FGFR2 were treated with 2 µM, 4 µM, or 6 µM dovitinib, corresponding to 5, 10, and 15-times the IC50, because, as noted above, N550K already imparts significant resistance to dovitinib in isolation. No resistant clones were isolated after dovitinib treatment in the N550K resistance screen.

Example 5

Figure 3:
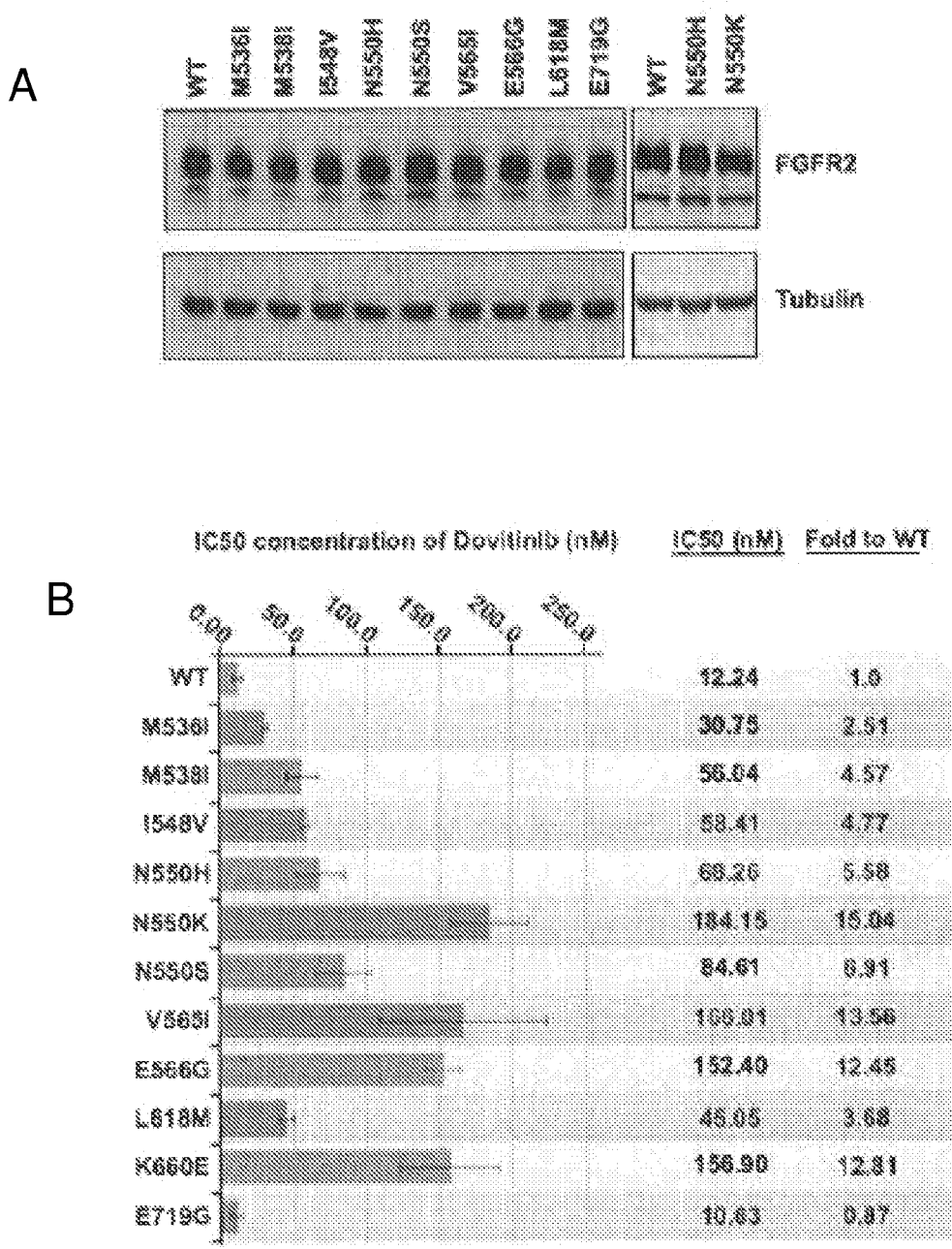
FIG. 3 depicts that the identified FGFR2 mutations confer dovitinib resistance in stable BaF3.FGFR2 cells. A shows the Western blot analysis of stable BaF3 cells expressing wild-type or mutant FGFR2 using an anti-FGFR2 antibody (BEK-C17) or anti-tubulin antibody as loading control. B shows the proliferation and IC50 of the stable BaF3-FGFR2 cells treated with dovitinib in different concentrations.

Reintroduction of the Mutations Confirmed the Identified Mutations Induce Dovitinib Resistance To confirm that the mutations identified in the BaF3 screen were sufficient to confer dovitinib-resistance, independent BaF3 cell lines stably expressing FGFR2 harboring the putative drug-resistant mutations identified in the initial BaF3 screen were generated (FIG. 3A). As the Y770fsX14 C-terminal deletion mapped away from the ATP-binding site and could not be identified with the C-terminal antibody that was used, this mutation was not assessed. The sensitivity of these stable cell lines to dovitinib was then measured by assessing cell viability at increasing dovitinib concentrations (FIG. 3B). As the activating N550K mutation was identified in the resistance screen, the sensitivity of the other major activating mutation seen in patients, K660E, was also assessed. All mutations with the exception of E719G led to drug resistance as manifested by 2.11 to 15.04-fold increases in IC50 value in comparison to wildtype FGFR2. The N550K, V565I, K660E and E566G mutations imparted the greatest magnitude of resistance (FIG. 3B). Dovitinib sensitivity of BaF3 cells expressing the E719G mutant FGFR2 was not significantly different than of those expressing wild-type FGFR2. The clone where the E719G mutation was identified also harbored an N550H mutation in FGFR2, so presumably the latter N550H mutation conveyed resistance in this clone and the E719G mutation represents a passenger mutation.

Example 6

Effect of Dovotinib on Phosphorylation of FGFR2 Mutants

Figure 4:
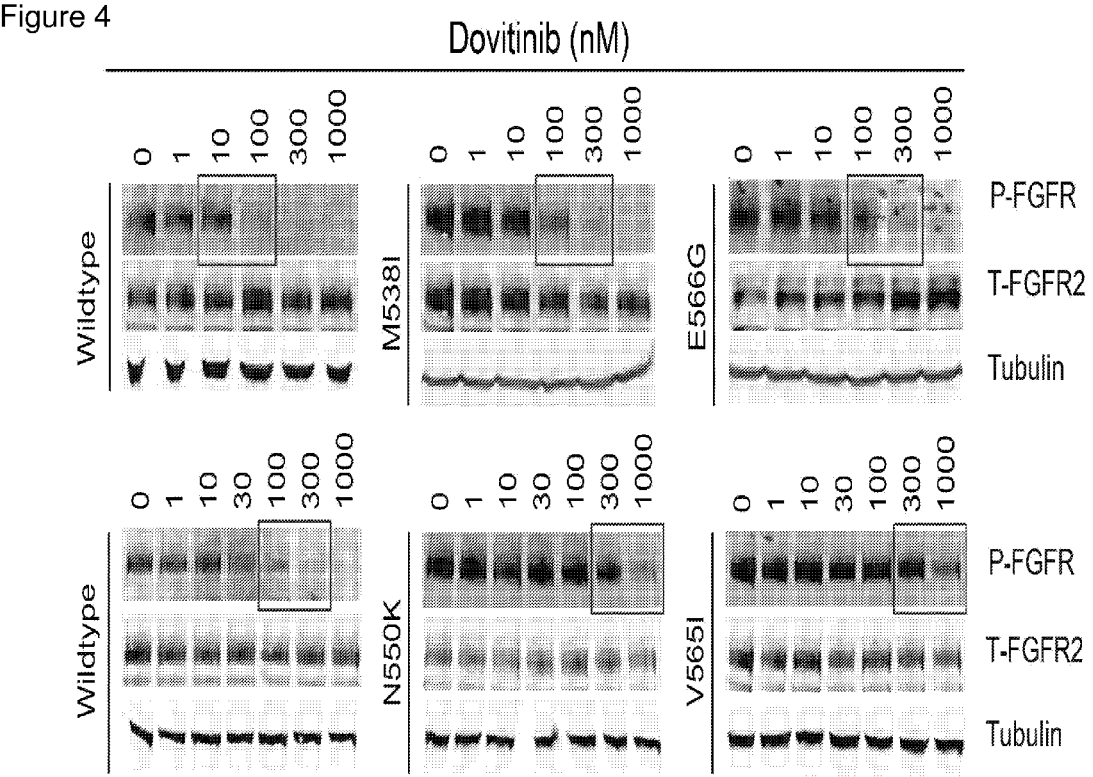
FIG. 4 depicts the dovitinib sensitivity in a panel of FGFR2 kinase resistance mutations. The phosphorylation status of FGFR2 was then assessed by Western blot.

The phosphorylation status of FGFR2 was also assessed in a panel of the identified mutations in response to dovitinib. The BaF3-FGFR cells were pre-treated for 2 hours with increasing Dovotinib concentrations followed by stimulation with FGF10/heparan sulfate. Following pre-treatment with increasing concentrations of dovitinib, BaF3-FGFR2 mutant (M538I, E566G, N550K and V565I) or wildtype cells were stimulated with FGF10/heparin sulfate. The phosphorylation status of FGFR2 was then assessed by western blot (FIG. 4). It was shown that FGFR2 mutants are more resistant to Dovotinib mediated inhibition of ligand-induced FGFR2 phosphorylation.

Example 7

Mutations Cause Cross-Resistance to PD173074 but not to Ponatinib

Figure 5:
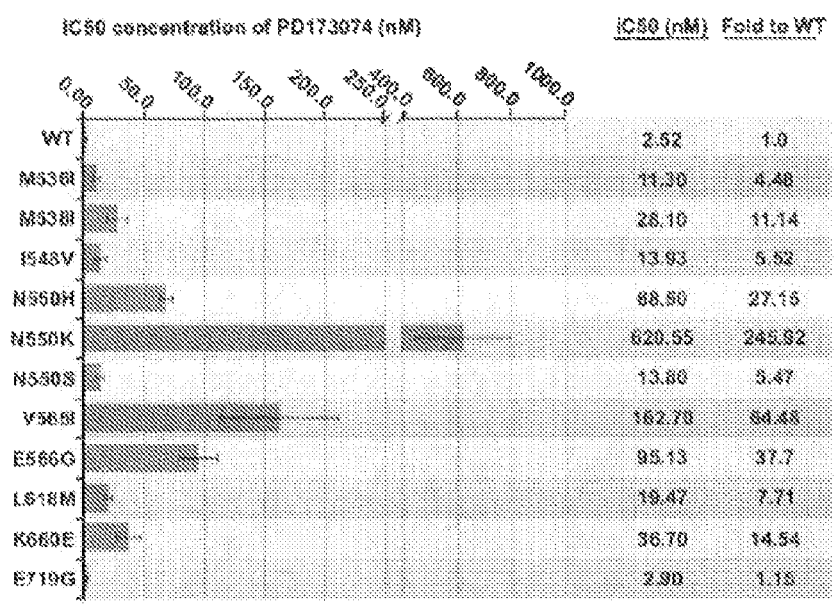
FIG. 5 depicts that dovitinib resistance mutations are similarly resistant to PD173074 but are almost all sensitive to ponatinib. A, proliferation was measured and IC50 was calculated for the stable BaF3-FGFR2 cells treated with PD173074 in concentrations ranging from 3 nM to 10 µM. B, proliferation was measured and IC50 was calculated for the stable BaF3-FGFR2 cells treated with 0.1 nM-1 µM of ponatinib.
Figure 5:
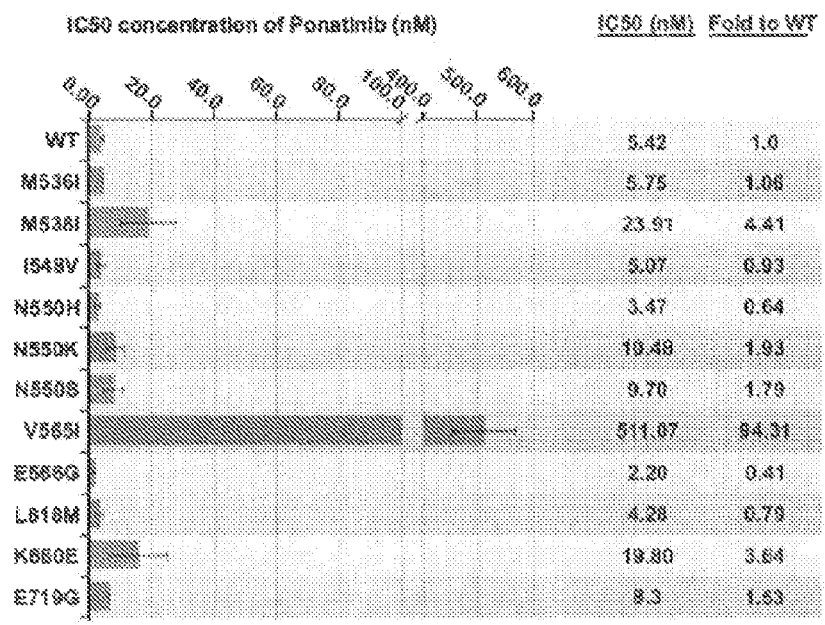

To examine whether the identified dovitinib-resistant FGFR2 mutations can also confer resistance to other FGFR inhibitors, ligand-induced proliferation of BaF3 cells expressing the drug-resistant FGFR2 was measured in the presence of PD173074 and ponatinib. As shown in FIG. 5A, the dovitinib-resistant mutations also imparted resistance to PD173074. As with dovitinib, the N550K molecular brake region mutation and the V565I gatekeeper mutation also caused greatest resistance towards PD173074. Interestingly, the N550K mutation provided considerably more resistance than N550H and N550S, perhaps indicating that the conformation of N550K provides resistance through another mechanism, in addition to loss of the molecular brake. In contrast, ponatinib effectively inhibited all the dovitinib-resistant FGFR2 mutants with the exception of the V565I gatekeeper mutant (FIG. 5B).

Figure 6:
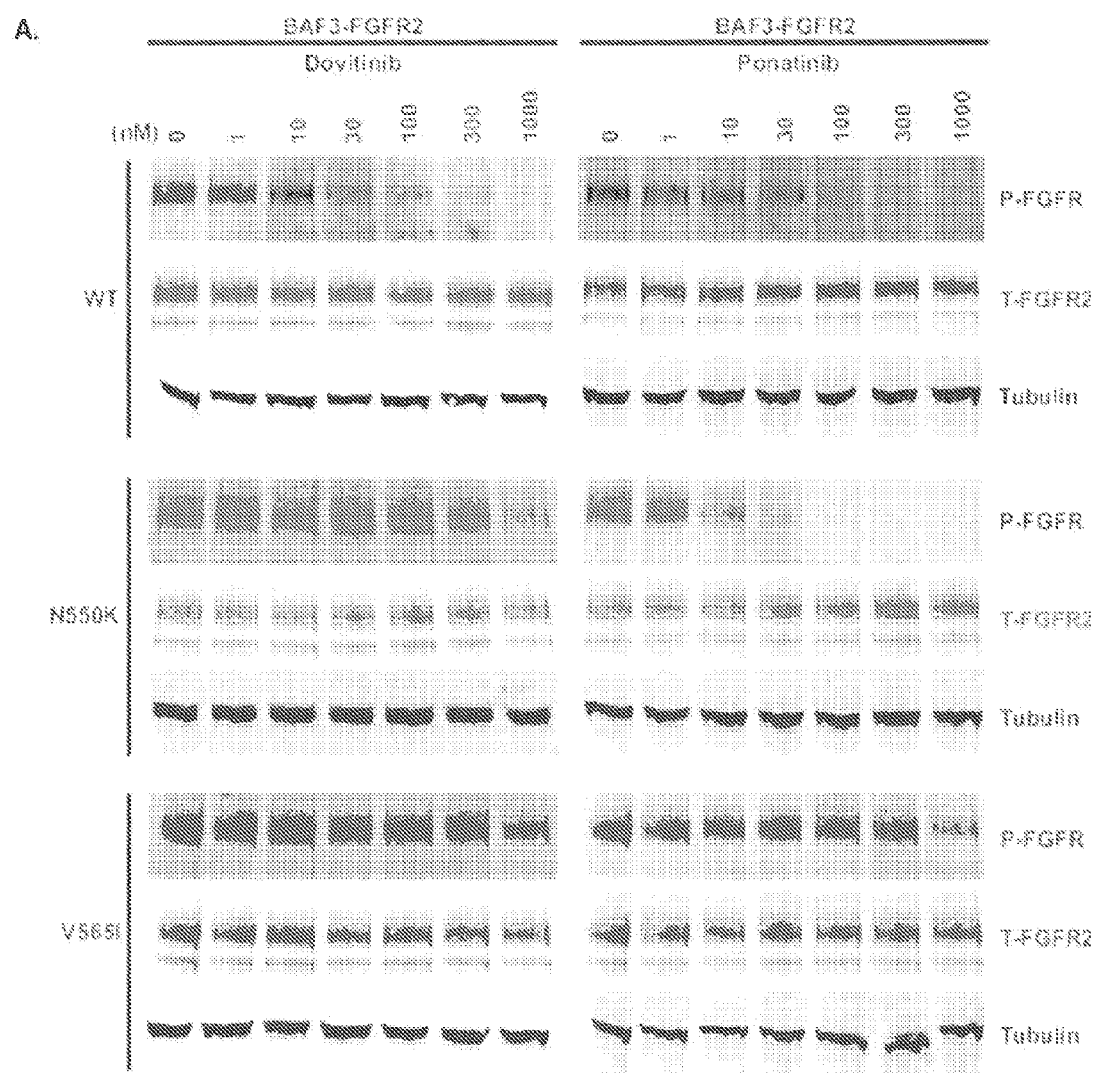
FIG. 6 depicts the change in FGFR2 phosphorylation in response to treatment with dovitinib and ponatinib. A, Western blot for the Stable BaF3.FGFR2 cells treated with dovitinib or ponatinib inhibitors using an anti pan-phospho-, anti-FGFR2 (BEK-C17) and anti-tubulin antibodies. B, Densitometry analysis of the change in phosphorylation due to pre-treatment with dovitinib and ponatinib.
Figure 6:
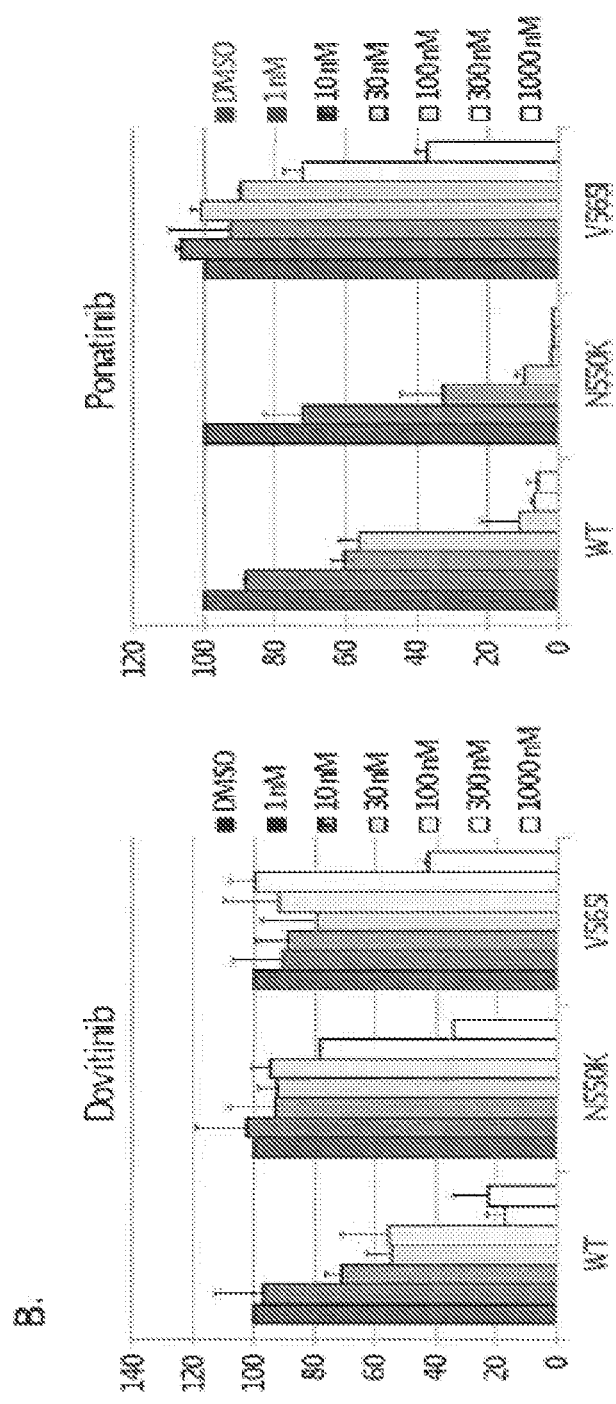

To further explore the differential sensitivity of ponatinib to the dovitinib resistant mutations, BaF3 cell lines expressing wild-type FGFR2b or N550K and V565I drug-resistant FGFR2b mutants were incubated with dovitinib or ponatinib followed by FGF10 ligand stimulation and the phosphorylation of FGFR2 was examined. Treatment with dovitinib reduced receptor phosphorylation in BaF3.FGFR2 wild-type cells to ~50% at a concentration of 52.1 nM (FIGS. 6A and 6B). In contrast, the concentration of dovitinib required to reduce receptor phosphorylation to ~50% in BaF3.FGFR2 N550K and BaF3.FGFR2 V565I cells, was 794 nM and 954 nM, respectively. Ponatinib inhibited phosphorylation of wild-type FGFR2b with an IC50 of 30.73 nM that is comparable to that of dovitinib. In stark contrast to dovitinib, ponatinib was highly effective in inhibiting the N550K FGFR2 mutant (IC50 of 5.72 nM), demonstrating the sensitivity of this FGFR2 mutant to ponatinib. Notably, the V565I gatekeeper mutant was still refractory to inhibition by ponatinib (IC50 661 nM), emphasizing the potency of this mutation to confer resistance to all three FGFR inhibitors.

Example 8

Effect of Ponatinib on Phosphorylation of FGFR2 Mutants

Figure 7:
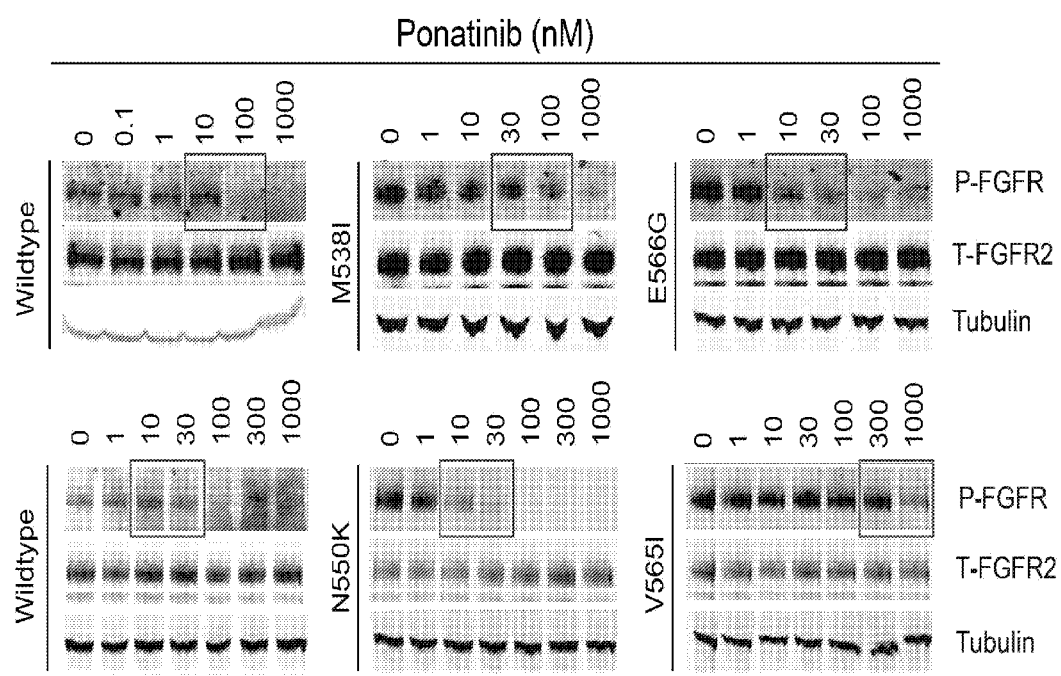
FIG. 7 depicts the ponatinib sensitivity in a panel of FGFR2 kinase resistance mutations, and the phosphorylation status of FGFR2 was then assessed by western blot.

The phosphorylation status of FGFR2 was also assessed in the obtained panel of the kinase mutations in response to Ponatinib. Following pre-treatment with increasing concentrations of Ponatinib, BaF3-FGFR2 mutant (N550K, V565I, M538I and E566G) or wildtype cells were stimulated with FGF10/heparan sulfate. The phosphorylation status of FGFR2 was then assessed by western blot (FIG. 7). It was shown that V565I "gatekeeper" mutation confers resistance to Ponatinib-mediated inhibition of ligand-induced FGFR2 phosphorylation.

Example 9

Endometrial Cancer Cell Lines Expressing Various FGFR2 Mutations (N550K, S252W and C383R) Demonstrate both Sensitivity and Intrinsic Resistance to FGFR Inhibition It was previously reported that the AN3CA and MFE296 cell lines, which carry the N550K FGFR2 mutation, are sensitive to FGFR inhibition with PD174074. To better gauge the relevance of the N550K mutation in resistance to FGFR inhibition in the correct cellular context, four additional cell lines were identified with mutations in FGFR2. It was hypothesized that a comparison of the mutant FGFR2 cell lines would show that all cell lines would be equally sensitive to ponatinib but that the N550K lines could show relative resistance to PD173074 and dovitinib (compared to cell lines carrying S252W and C383R FGFR2 mutations). Sensitivity across the panel was in the order ponatinib (most sensitive), then dovitinib, then PD173074 (least sensitive). Ponatinib was more potent than the other FGFR inhibitors in both the FGFR2 mutant and FGFR2 wild-type cell lines (e.g. Ishikawa) suggesting its increased potency was not only due to its ability to bind the active FGFR2 but also due to its multi-kinase nature. Within the FGFR2 mutant cell lines, 3/7 showed marked resistance to PD173074 (IC50>4 µM) including EI, EJ and EN1078D. With the exception of EN1078D treated with dovitinib, these three FGFR2 mutant cell lines also showed relative resistance to dovitinib and ponatinib when compared to the average IC50 of the three most sensitive cell lines versus that of the three FGFR2 wild-type cell lines. As the same cell lines showed similar relative resistance to PD173074, dovitinib and ponatinib it suggests these cell lines have intrinsic resistance to FGFR inhibition that is not overcome by an inhibitor that is capable of binding to the active conformation of the kinase.

Example 10

Stable Expression of N550K Mutant FGFR2 in Inhibitor Sensitive JHUEM-2 Cells Confers Resistance to PD173074

Figure 8:
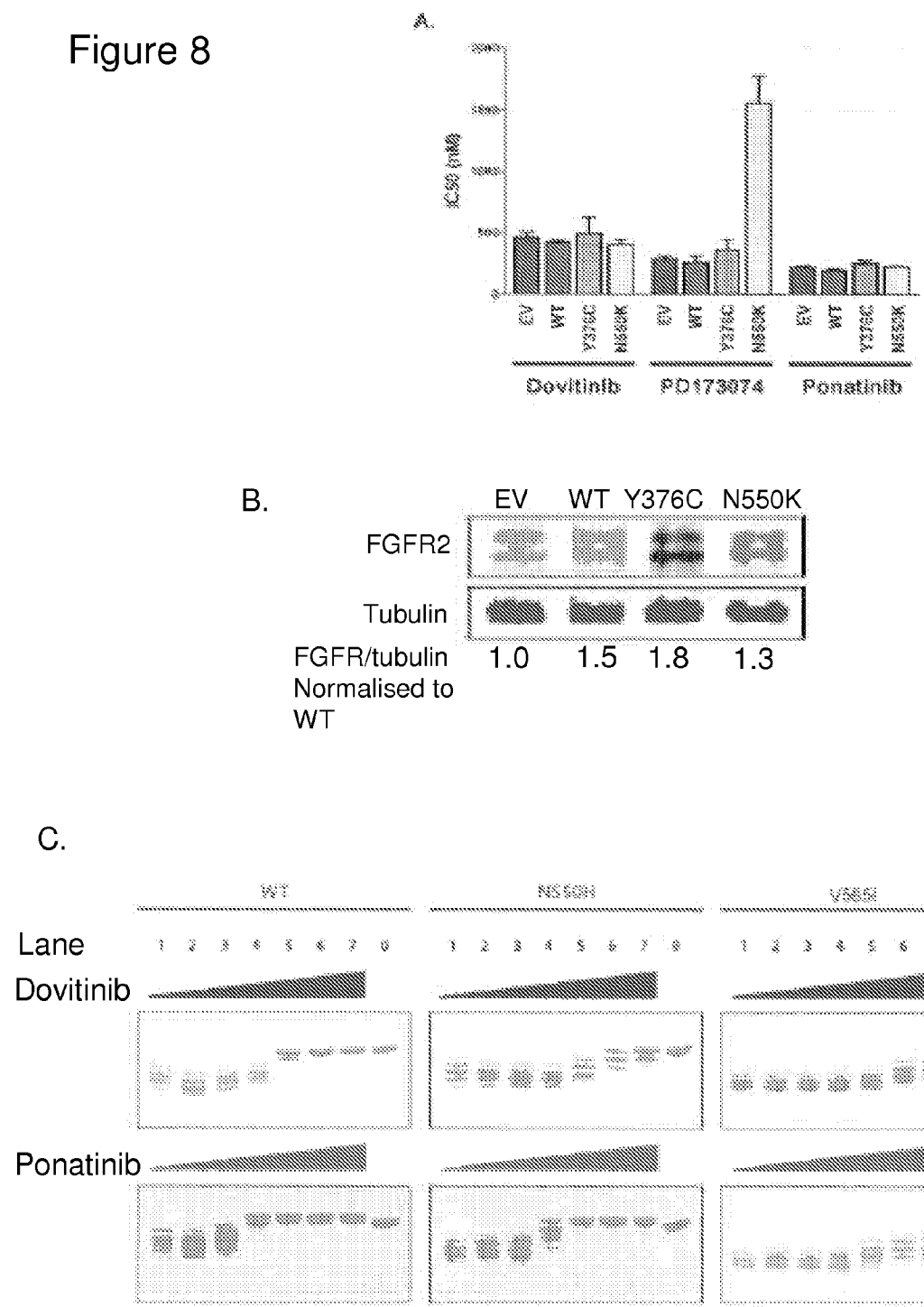
FIG. 8 depicts that the N550K mutation confers resistance to PD173074, but not dovitinib or ponatinib, when expressed in FGFR inhibitor sensitive JHUEM-2 cells. A, proliferation was measured and IC50 was calculated for the stably trans- fected JHUEM-2 cells were treated with dovitinib, PD173074 and ponatinib in increasing concentrations from 1 nM to 10 µM. B, Western blots demonstrating FGFR2 expression levels in stably transfected JHUEM-2 lines. EV, empty vector; WT, wild-type. C, Both dovitinib and ponatinib are potent inhibitors of the wild-type FGFR2 kinase whereas only ponatinib effectively inhibits the N550H mutant FGFR2. Neither dovitinib nor ponatinib is capable of inhibiting the V565I "gatekeeper" mutant. The control lane 1 shows extent of phosphorylation in the absence of inhibitors. In lanes 2 to 7, increasing concentrations of inhibitors were added into the autophosphorylation reactions to inhibit the kinase autophosphorylation. The kinase:inhibitor molar ratios of lane 2 to 7 are 1:0.2, 1:0.5, 1:1, 1:2, 1:5 and 1:10 respectively. The control lane 0 is the kinase in the absence of ATP: MgCl2.

As those endometrial cancer cell lines carrying the N550K mutation had a diverse response to FGFR inhibition (presumably reflecting the acquisition of additional genetic/epigenetic changes), an alternative approach was sought to confirm whether FGFR2N550K is a true resistance mutation. The sensitive JHUEM-2 cell line (FGFR2C383R) was stably transfected with FGFR2N550K. JHUEM-2 cells stably expressing an empty vector control, wild-type FGFR2 and an extracellular domain activating FGFR2 mutant (Y376C) were also created. The cell viability of these lines in response to FGFR inhibition with dovitinib, PD173074 and ponatinib was then measured. Although expression of FGFR2N550K did not affect the sensitivity of JHUEM-2 cells to dovitinib and ponatinib, it did however cause a ~5 fold increase in the IC50 to PD173074 (FIG. 8A). As demonstrated in FIG. 8B, all three wild-type and mutant FGFR2 transfected cell lines express higher levels of FGFR2 than the empty vector control line. Indeed the FGFR2N550K expressing cells expressed less FGFR2 than the FGFR2Y376C cell line, and yet only the FGFR2N550K cells showed increased resistance to PD173074. While N550K did not confer resistance to dovitinib and ponatinib when expressed at low levels in JHUEM cells, it was confirmed that N550H imparts resistance to dovitinib using in vitro kinase assays (FIG. 8C). Similar to the N550H/K-expressing BaF3 cells, in vitro kinase assays showed that N550H was more sensitive to ponatinib than dovitinib. Specifically dovitinib and ponatinib could inhibit the kinase activity of WT FGFR2 when mixed at a kinase: inhibitor molar ratio of 1:2. Ponatinib could inhibit N550H at a similar molar ratio whereas dovitinib could not provide the same inhibition even at a molar ratio of 1:10. The kinase activity of the V565I mutant was resistant to both dovitinib and ponatinib even when mixed at a molar ratio of 1:10. These results confirm the BaF3 data showing that ponatinib is more effective than dovitinib at inhibiting FGFR2N550K and that the V565I gatekeeper mutant is resistant to both dovitinib and ponatinib. Taken together this confirms the BaF3 data that FGFR2N550K is indeed a true resistance mutation.

Example 11

Figure 9:
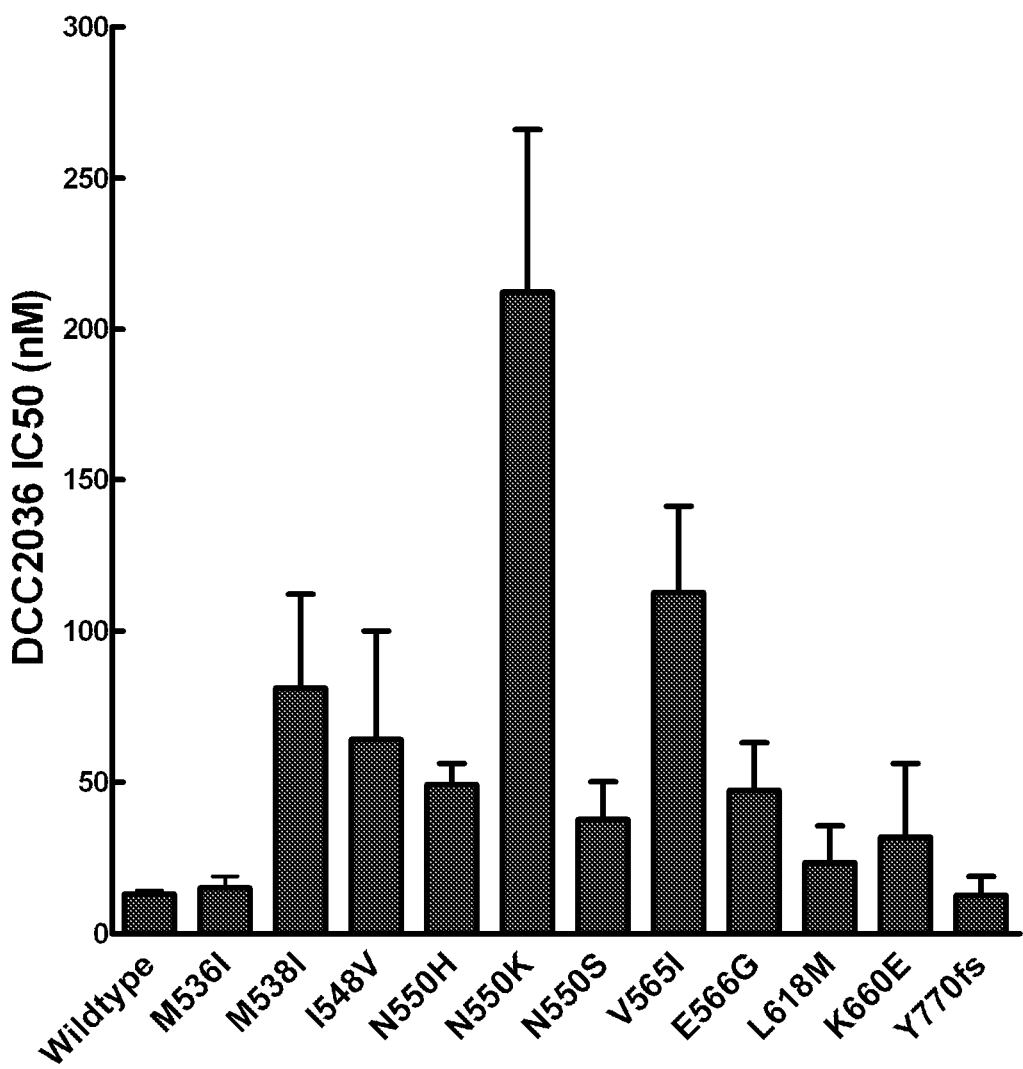
FIG. 9 depicts the DCC2036 sensitivity in a panel of FGFR2 kinase resistance mutations, and most mutations except N550K are sensitive to DCC2036.

Examine the Efficacy of Other Emerging Anti-FGFR Agents (DCC2036, BGJ398, AZD4547) against the Panel of Dovitinib Resistant Mutations DCC2036 is a multi-kinase inhibitor that targets active conformation of kinase. It is a "switch pocket" inhibitor rather than ATP-competitive inhibitor. DCC2036 inhibit a kinase by preventing "activation loop" binding to the "switch pocket", and thus turning on a kinase or can even turn off an already activated kinase. As shown in Figure (FIG. 9), most FGFR2 kinase mutations except N550K from this BaF3 resistance screen are sensitive to DCC2036.

Figure 10:
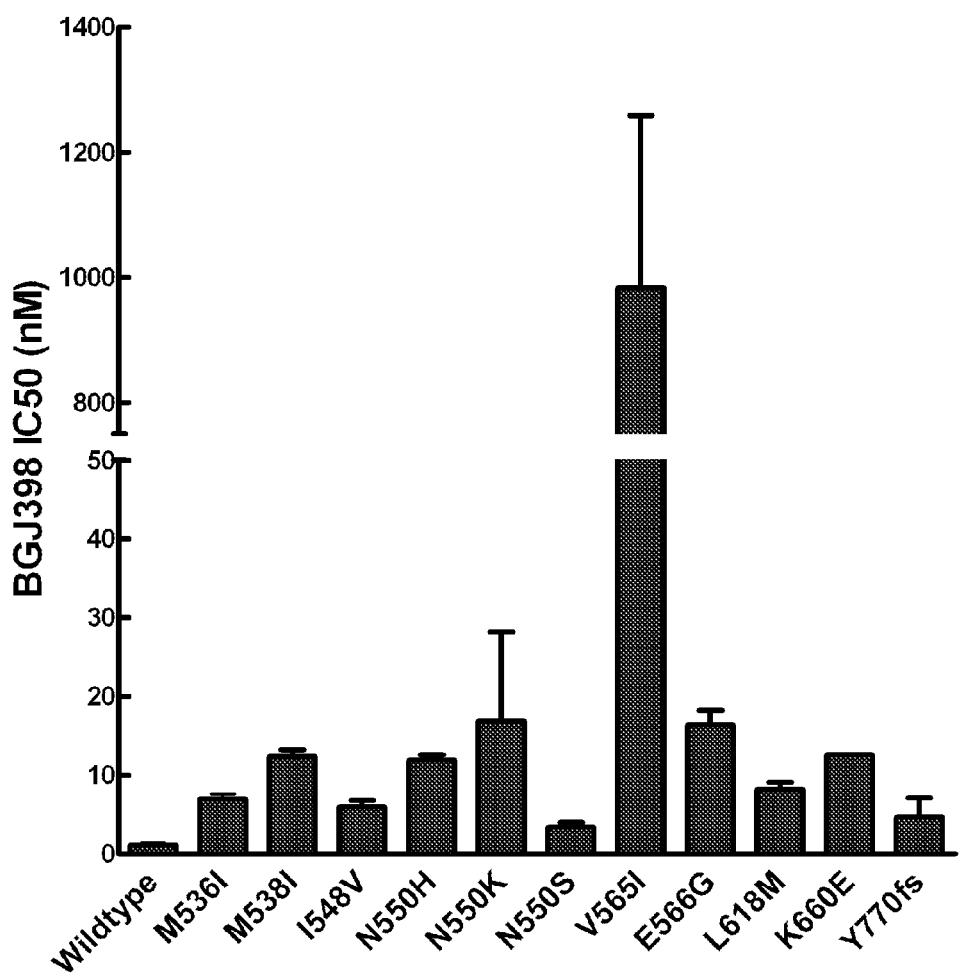
FIG. 10 depicts the BGJ398 sensitivity in a panel of FGFR2 kinase resistance mutations, and all mutations except V565I are sensitive to BGJ398.

BGJ398 is a pan-FGFR inhibitor. The cell viability of the panel of mutant lines in response to FGFR inhibition with BGJ398 was then measured. As shown in Figure (FIG. 10), most mutations presented more resistance to BGJ398 than wildtype, particularly V565I. Therefore, all FGFR2 kinase mutations except the V565I from the mutation panel are sensitive to BGJ398. In addition, BGJ398 showed good activity against N550K and other activating mutations, such as K660E.

Figure 11:
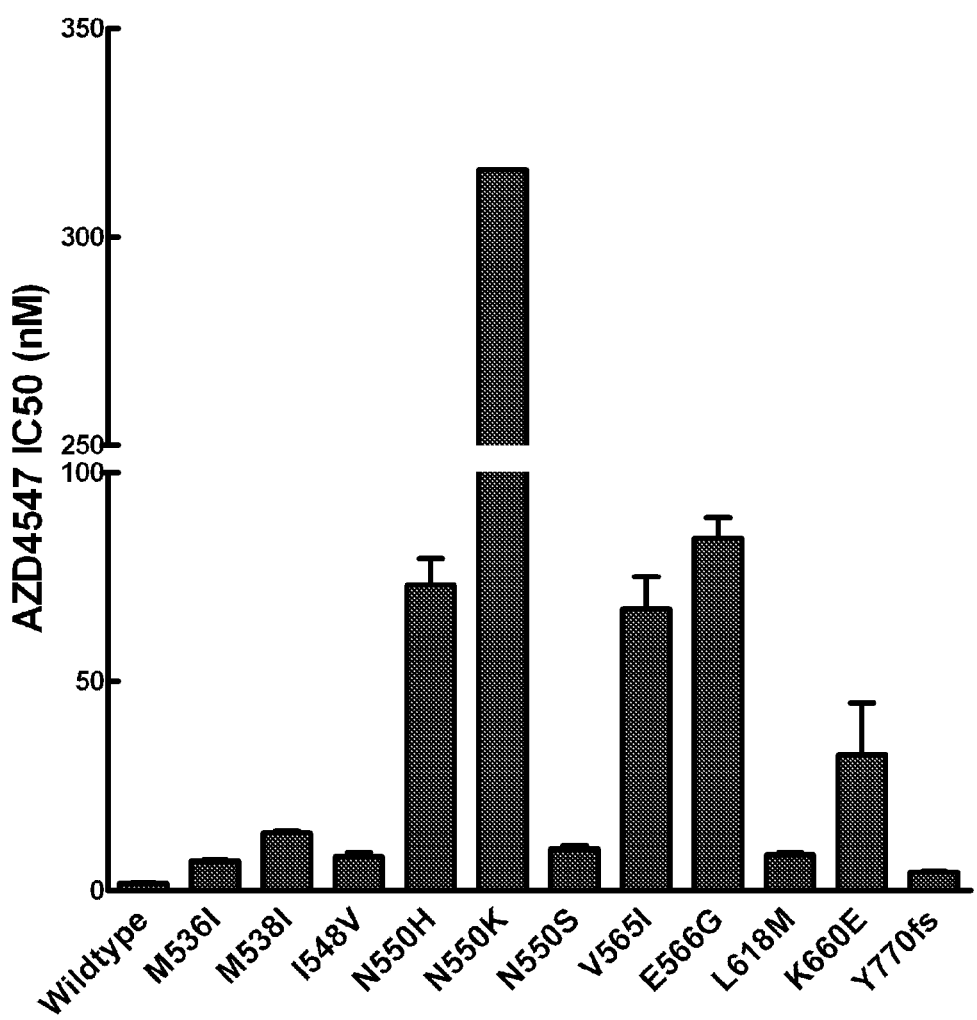
FIG. 11 depicts the AZD4547 sensitivity in a panel of FGFR2 kinase resistance mutations, and most mutations are refractory to AZD4547, except V565I demonstrates some sensitivity.

AZD4547 is another specific pan-FGFR inhibitor. The cell viability of the panel of mutant lines in response to FGFR inhibition with AZD4547 was then measured. As shown in Figure (FIG. 11), most mutations presented more resistance to AZD4547 than wildtype, particularly N550K. Most activating FGFR2 kinase mutations from the BaF3 resistance screen are refractory to AZD4547. But AZD4547 demonstrates some activity against V565I "gatekeeper" mutation.

Therefore, the above examples show that N550K mutations are present in endometrial cancer (~25% of FGFR2 mutations). However, Ponatinib and BGJ398 are likely to be efficacious in EC patients with N550K mutations; whereas AZD4547 and DCC2036 likely to be efficacious in patients who develop V565I "gatekeeper" resistance mutations. This finding has important impact on clinical trials and patient selection, and in personalized medicine for cancer treatment using specific and responsive FGFR inhibitors.

The foregoing description of a preferred embodiment and best mode of the invention known to the applicant at this time of filing the application has been presented and is intended for the purposes of illustration and description. It is not intended to be exhaustive or limit the invention to the precise form disclosed and many modifications and variations are possible in the light of the above teachings. The embodiment was chosen and described in order to best explain the principles of the invention and its practical application and to enable others skilled in the art to best utilize the invention in various embodiments and with various modifications as are suited to the particular use contemplated. Therefore, it is intended that the invention not be limited to the particular embodiments disclosed for carrying out this invention, but that the invention will include all embodiments falling within the scope of the appended claims.

What is claimed is:

1. A method for treating a subject having a cancer with amplified or mutationally activated FGFR2 (fibroblast growth factor receptor) kinase, comprising:
   receiving a sample from the subject;
   analyzing the sample for the presence of at least one FGFR2 kinase mutation variant;
   wherein the subject is drug resistant to one or more FGFR2 kinase inhibitors if one or more FGFR2 kinase mutation variants selected from the group consisting of M536I, M538I, I548V, N550H, N550K, N550S, V565I, E566G, L618M, E719G, and Y770IfsX14 is present in the sample from the subject, wherein the FGFR2 kinase inhibitor is selected from the group consisting of dovitinib, PD173073, AZD4547, ponatinib, BGJ398, and DCC2036; and
   administering a regimen comprising ponatinib and/or BGJ398 to the subject if at least N550K mutation is present in the patient; or
   administering a regimen comprising AZD4547 and/or DCC2036 to the subject if at least V565I mutation is present in the subject.

2. The method of claim 1, wherein the sample comprises a tumor cell.

3. The method of claim 2, wherein the tumor cell is of a type dependent on FGFR activity.

4. The method of claim 3, wherein the tumor cell is an endometrial cancer cell.

5. The method of claim 1, wherein the sample is selected from the group consisting of a biopsy, a tissue, a body fluid, and a single cell, comprising tumor DNA, RNA, protein, peptide or fragments thereof.

6. The method of claim 1, wherein the presence of at least one FGFR2 kinase mutation variant in the sample is determined by a technique selected from the group consisting of PCR, RT-PCR, sequencing, hybridization, microarray genotyping, HPLC, Mass Spectrometry, and antibody-based immunoassays.

7. A method for determining whether a subject having cancer with amplified or mutationally activated FGFR2 is drug resistant to one or more FGFR2 kinase inhibitors, comprising
   receiving a sample from the subject;
   analyzing the sample for the presence of at least one FGFR2 kinase mutation variant selected from the group consisting of M536I, M538I, I548V, N550H, N550K, N550S, V565I, E566G, L618M, E719G, and Y770IfsX14;
   wherein the subject drug resistant to one or more FGFR2 kinase inhibitors if one or more FGFR2 mutation variants is present in the sample from the subject; and
   further wherein the FGFR2 kinase inhibitor is selected from the group consisting of dovitinib, PD173073, AZD4547, ponatinib, BGJ398, and DCC2036.

8. The method of claim 7, wherein the presence of N550K FGFR2 kinase mutation variant is associated with the drug resistance to dovitinib and AZD4547 in the subject.

9. The method of claim 7, wherein the presence of N550K FGFR2 kinase mutation variant is associated with the drug sensitivity to ponatinib and/or BGJ398 in the subject.

10. The method of claim 7, wherein the presence of V565I FGFR2 kinase mutation variant is associated with the drug sensitivity to AZD4547 and/or DCC2036 in the subject.

11. The method of claim 7, wherein the sample is selected from the group consisting of a biopsy, a tissue, a body fluid, and a single cell, comprising tumor DNA, RNA, protein, peptide or fragments thereof.

12. The method of claim 7, wherein the presence of at least one FGFR2 kinase mutation variant in the sample is determined by a technique selected from the group consisting of PCR, RT-PCR, sequencing, hybridization, microarray genotyping, HPLC, Mass Spectrometry, and antibody-based immunoassays.

* * * * *